United States Patent
Joy et al.

(10) Patent No.: US 9,353,214 B2
(45) Date of Patent: May 31, 2016

(54) SUBSTITUTED PHENACYL MOLECULES AND PHOTORESPONSIVE POLYMERS

(71) Applicant: The University of Akron, Akron, OH (US)

(72) Inventors: Abraham Joy, Copley, OH (US); Shuangyi Sun, Akron, OH (US)

(73) Assignee: The University of Akron, Akron, OH (US)

( * ) Notice: Subject to any disclaimer, the term of this patent is extended or adjusted under 35 U.S.C. 154(b) by 4 days.

(21) Appl. No.: 14/359,693

(22) PCT Filed: Dec. 17, 2012

(86) PCT No.: PCT/US2012/070060
§ 371 (c)(1),
(2) Date: May 21, 2014

(87) PCT Pub. No.: WO2013/090892
PCT Pub. Date: Jun. 20, 2013

(65) Prior Publication Data
US 2014/0323664 A1    Oct. 30, 2014

Related U.S. Application Data

(60) Provisional application No. 61/576,527, filed on Dec. 16, 2011.

(51) Int. Cl.
| | | |
|---|---|---|
| *C07C 49/245* | (2006.01) | |
| *C08G 63/664* | (2006.01) | |
| *C08G 64/04* | (2006.01) | |
| *C08G 63/02* | (2006.01) | |
| *C08G 63/06* | (2006.01) | |
| *C08G 63/19* | (2006.01) | |
| *C08G 64/06* | (2006.01) | |
| *C08F 26/06* | (2006.01) | |
| *C08G 64/16* | (2006.01) | |

(52) U.S. Cl.
CPC ............ *C08G 63/664* (2013.01); *C07C 49/245* (2013.01); *C08F 26/06* (2013.01); *C08G 63/02* (2013.01); *C08G 63/06* (2013.01); *C08G 63/19* (2013.01); *C08G 64/04* (2013.01); *C08G 64/06* (2013.01); *C08G 64/16* (2013.01)

(58) Field of Classification Search
None
See application file for complete search history.

(56) References Cited

U.S. PATENT DOCUMENTS

| | | | |
|---|---|---|---|
| 4,190,671 A | 2/1980 | Vanstone et al. | |
| 4,321,118 A * | 3/1982 | Felder | C07C 49/747 430/281.1 |
| 5,739,175 A * | 4/1998 | Nohr | C07C 51/373 522/34 |
| 2001/0007880 A1* | 7/2001 | Marchin | C07C 49/796 522/35 |
| 2002/0012873 A1 | 1/2002 | Jung et al. | |
| 2004/0096663 A1* | 5/2004 | Yamaguchi | C08F 283/12 428/403 |
| 2006/0268083 A1* | 11/2006 | Kunita | C09D 11/101 347/96 |

* cited by examiner

*Primary Examiner* — Robert C Boyle
(74) *Attorney, Agent, or Firm* — Renner Kenner Greive Bobak Taylor & Weber

(57) ABSTRACT

Substituted phenacyl molecules are provided and employed to create molecules and polymers/copolymers that exhibit photoresponsiveness. In some instances, the substituted phenacyl molecule is incorporated into the polymer/copolymer backbone, and photoirradiation of the polymer/copolymer causes the substituted phenacyl group to break down and the polymer/copolymer to undergo degradation. In other instances, the substituted phenacyl molecules extend as a side chain from the polymer/copolymer backbone. In yet other instances the substituted phenacyl molecules extend as a side chain from the polymer/copolymer backbone, and a drug or polymer additive is linked to the photoresponsive substituted phenacyl group such that photoirradiation releases the drug or additive. In yet other embodiments the substituted phenacyl molecules extend as a side chain from the polymer/copolymer backbone, and serve to link the polymer/copolymer to another polymer/copolymer backbone, and photoirradiation breaks the links.

22 Claims, 6 Drawing Sheets

SUBSTITUTED PHENACYL MOLECULES AND PHOTORESPONSIVE POLYMERS

CROSS-REFERENCE TO RELATED APPLICATIONS

This application claims the benefit of U.S. Provisional Application No. 61/576,527, filed Dec. 16, 2011.

FIELD OF THE INVENTION

The present invention generally relates to photoresponsive molecules and photoresponsive polymers and methods of making them.

BACKGROUND OF THE INVENTION

Photoresponsive polymers are being found to have several advantageous applications. Photoactivation can be used to control various polymer properties such as release or capture of additives, light activated bending, modulation of refractive index, or phase behavior. Some photoresponsive polymers are photodegradable, wherein photoactivation causes polymer backbone scission, thus decreasing the environmental burden of products made by such polymers. Photodegradable copolymers of vinylic monomers and carbon monoxide are commercially available and are used mostly in agricultural applications. In addition, over the past decade or so several photodegradable polymers have been designed, including polymers containing in-chain metal-metal bonds, photolabile dendrimers, and copolymers of methymethacrylate.

Currently there is a strong need in biomedical applications for polymers that are both photodegradable and biodegradable. Polymers with such properties would be responsive to photochemical input and at a later stage undergo hydrolysis in an aqueous biological environment. Such materials are being investigated as drug delivery devices and as platforms with photo-tunable physical and mechanical properties. Anseth et al have proposed nitrobenzyl ether based PEG hydrogel systems whose moduli and the resultant effect on cell behavior can be tuned by photoirradiation (Kloxin, A. M.; Kasko, A. M.; Salinas, C. N.; Anseth, K. S. Science 2009, 324, 59). Kasko et al. have synthesized hydrogels that are amenable to creating positive and negative features by two photon irradiation (Wong, D. Y.; Griffin, D. R.; Reed, J.; Kasko, A. M. Macromolecules 2010, 43, 2824). Zhao et al. reported a micellar system from nitrobenzyl ether based polyurethanes that degrades upon photoirradiation (Han, D. H.; Tong, X.; Zhao, Y. Macromolecules 2011, 44, 437). Almutairi has reported a quinone methide nanoparticle system that upon light activation results in a cascade of cyclization and rearrangement reactions resulting in degradation of the polymer ((a) Almutairi et al., A. Macromolecules 2011, 44, 8590, (b) Fomina et al. A. J Am Chem Soc 2010, 132, 9540). These examples point to the advantages of photoresponsive polymers. The present invention adds to this general portfolio of photoactive materials to address the increasing need for photoresponsive materials.

SUMMARY OF THE INVENTION

A first embodiment of this invention provides a substituted phenacyl composition of matter according to the following structure:

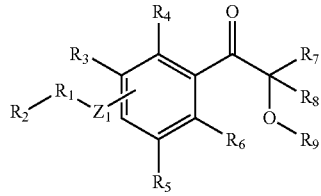

wherein $R_1$ is an alkyl chain of from C1 to C10; $R_2$ is a group of atoms containing at least one functional group; $R_3$, $R_4$, $R_5$, $R_6$, $R_7$, $R_8$ and $R_9$ are selected from any atom or group of atoms, and $Z_1$ may be at the ortho-, meta- or para-position and is selected from O, S, HNC=O or $R_{10}$NC=O, wherein $R_{10}$ is selected from any atom or group of atoms.

A second embodiment of this invention provides a composition as in the first embodiment, wherein $Z_1$ is at the para-position.

A third embodiment of this invention provides a coposition as in either the first or second embodiment, wherein $R_2$ is selected from a carboxyl group, a hydroxyl group and a vinyl group.

A fourth embodiment of this invention provides a composition as in any of the first through third embodiments, wherein $R_3$ through $R_9$ are selected from H, Cl, Br, F, alkyl, vinyl, alkynyl, aryl, or alkoxy groups.

A fifth embodiment of this invention provides a composition as in any of the first through fourth embodiments, wherein $R_3$ through $R_9$ are hydrogen.

A sixth embodiment of this invention provides a composition as in any of the first through fifth embodiments, wherein $R_1$ is a propylene chain, $R_2$ is an hydroxyl group and $Z_1$ is oxygen, the substituted phenacyl composition of matter having the formula:

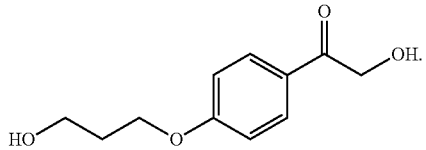 [SMILES: O=C(CO)c1ccc(OCCCO)cc1]

A seventh embodiment of this invention provides a composition as in any of the first through sixth embodiments, wherein $R_1$ an alkyl chain of from C1 to C10, $R_2$ is —COOH, and $Z_1$ is oxygen.

An eighth embodiment of this invention provides a composition as in any of the first through seventh embodiments, wherein $R_1$ is $CH_2$.

A ninth embodiment of this invention provides a composition as in any of the first through eighth embodiments wherein $R_3$ through $R_8$ are selected from H, Cl, Br, F, alkyl, vinyl, alkynyl, aryl, or alkoxy groups, O—$R_9$ is selected from an ester group, a carbonate group, a phosphate group, a sulfate group and sulfinate group.

A tenth embodiment of this invention provides a composition of matter selected from a polymer, macromolecule, copolymer, oligmer, dendrimer, dendron, and macrocycle, the composition comprising one or more following structural unit(s):

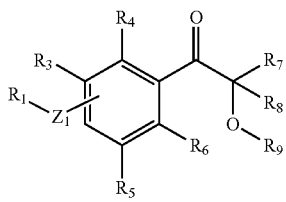

wherein $R_1$ is a bond or an alkyl chain of from C1 to C10; $R_3$, $R_4$, $R_5$, $R_6$, $R_7$, $R_8$, and $R_9$ may be any atom or group of atoms; $Z_1$ may be at the ortho, meta or para position and is selected from O, S, HNC=O or $R_{10}$NC=O, wherein $R_{10}$ is selected from any atom or group of atoms.

An eleventh embodiment of this invention provides a composition as in the tenth embodiment, wherein $R_9$ is selected from RC=O, wherein R represents any substitution.

A twelfth embodiment of this invention provides a composition as in the tenth or eleventh embodiment, wherein O—$R_9$ is selected from an ester group, a carbonate group, a phosphate group, a sulfate group and sulfinate group.

A thirteenth embodiment of this invention provides a composition as in any of the tenth through twelfth embodiments, wherein $R_3$ through $R_8$ are hydrogen, and $Z_1$ is oxygen and is at the para position.

A fourteenth embodiment of this invention provides a composition as in any of the tenth through thirteenth embodiments, wherein the composition is a polycarbonate homopolymer having the following structure:

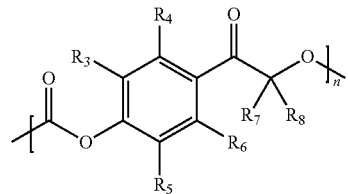

wherein $R_3$ through $R_8$ may be any atom or group of atoms and n is any number of repeating units.

A fifteenth embodiment of this invention provides a composition as in any of the tenth through fourteenth embodiments, wherein $R_3$ through $R_8$ are hydrogen.

A sixteenth embodiment of this invention provides a composition as in any of the tenth through fifteenth embodiments, wherein the composition is a polycarbonate polymer having the following structure:

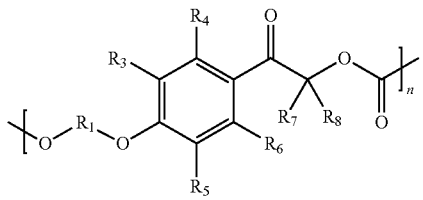

wherein $R_1$ is alkyl chain of from C1 to C10; $R_3$, $R_4$, $R_5$, $R_6$, $R_7$, and $R_8$ may be any atom or group of atoms, n is any number of repeating units.

A seventeenth embodiment of this invention provides a composition as in any of the tenth through sixteenth embodiments, wherein $R_1$ is a propylene chain ($C_3H_6$) and $R_3$ through $R_8$ are hydrogen.

An eighteenth embodiment of this invention provides a composition as in any of the tenth through seventeenth embodiments, wherein the composition is a polycarbonate copolymer having the following structure:

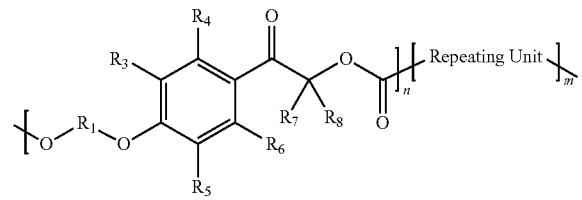

wherein R1 is alkyl chain of from C1 to C10; R3, R4, R5, R6, R7, and R8 may be any atom or group of atoms; n is any number of repeating units; "Repeating Unit" is a repeating unit contributed by a comonomer or copolymer; m is any number of repeating units; wherein the n and m repeating units are in statistical arrangement.

A nineteenth embodiment of this invention provides a composition as in any of the tenth through eighteenth embodiments, wherein $R_1$ is a propylene chain ($C_3H_6$) and $R_3$ through $R_8$ are hydrogen.

A twentieth embodiment of this invention provides a composition as in any of the tenth through nineteenth embodiments, wherein the composition is a polyester polymer comprising the following structure:

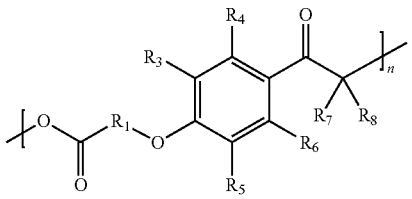

wherein $R_3$, $R_4$, $R_5$, $R_6$, $R_7$, and $R_8$ may be any atom or group of atoms, $R_1$ is an alkyl chain of from C1 or more to C10 or less, and n represents any number of repeating units.

A twenty-first embodiment of this invention provides a composition as in any of the tenth through twentieth embodiments, wherein $R_3$ through $R_8$ are hydrogen and $R_1$ is methylene ($CH_2$)

A twenty-second embodiment of this invention provides a composition as in any of the tenth through twenty-first embodiments, wherein the polymer is a copolymer comprising the structure thereof as part of the polymer.

A twenty-third embodiment of this invention provides a composition as in any of the tenth through twenty-second embodiments, wherein the composition is a polyester polymer comprising the following structure:

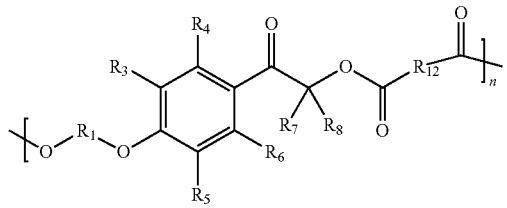

wherein $R_3$, $R_4$, $R_5$, $R_6$, $R_7$, and $R_8$ may be any atom or group of atoms, $R_1$ is an alkyl chain of from C1 to C10, $R_{12}$ is either a bond between the two carbonyl groups or is an alkyl chain of from C1 to C10, and n is any number of repeating units.

A twenty-fourth embodiment of this invention provides a composition as in any of the tenth through twenty-third embodiments, wherein $R_3$ through $R_8$ are hydrogen, $R_1$ is a propylene chain ($C_3H_6$) and $R_{12}$ is a butylene chain ($C_4H_8$).

A twenty-fifth embodiment of this invention provides a composition as in any of the tenth through twenty-third embodiments, wherein the polymer is a copolymer comprising the structure thereof as part of the polymer.

A twenty-sixth embodiment of this invention provides a composition as in any of the tenth through twenty-third embodiments, wherein $R_1$ links the structural unit thereof to a polymer chain, and $R_9$ is part of a drug molecule, part of an additive, or part of a sensitizer.

A twenty-seventh embodiment of this invention provides a composition as in any of the tenth through twenty-third embodiments, wherein $R_1$ and $R_9$ individually links the structural unit thereof to a polymer chain, and the structural unit thereof serves as a linker of the polymer chains, wherein the polymer chains could be same or different.

DETAILED DESCRIPTION OF ILLUSTRATIVE EMBODIMENTS

Figure 1:
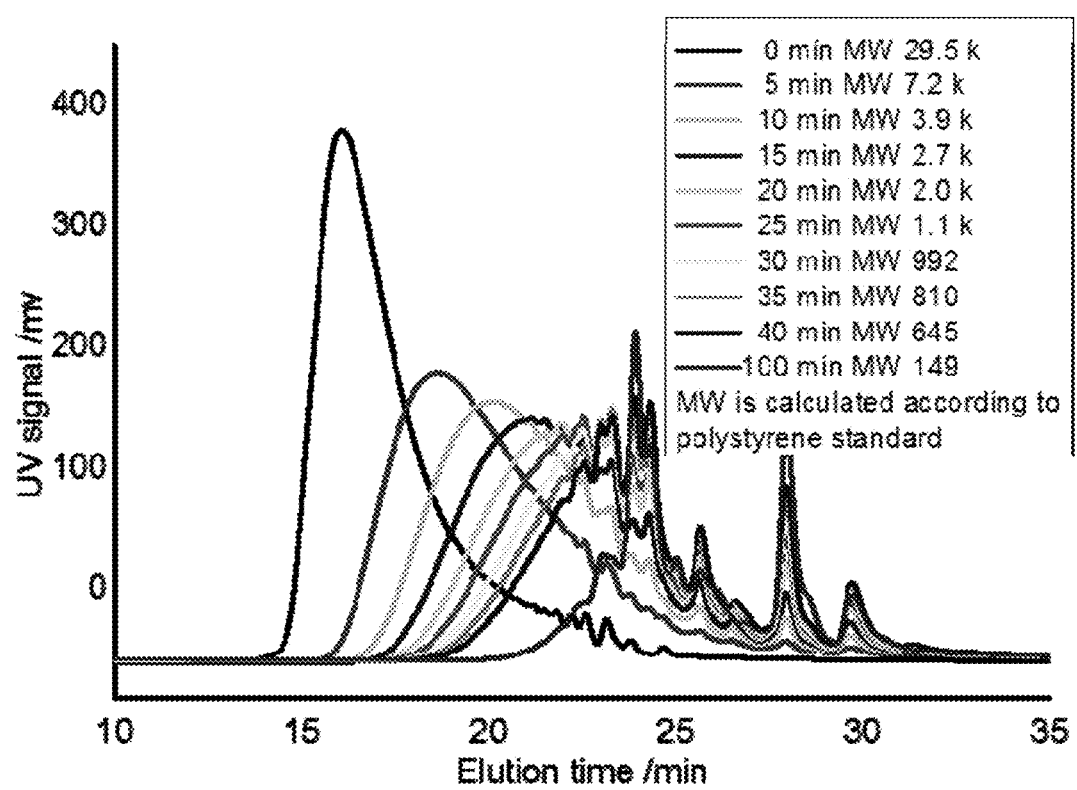
FIG. 1 is a graph of gel permeation chromatograph (GPC) traces of irradiated samples of the homopolymer 15 showing decrease in molecular weight (MW) with increasing irradiation time
Figure 2:
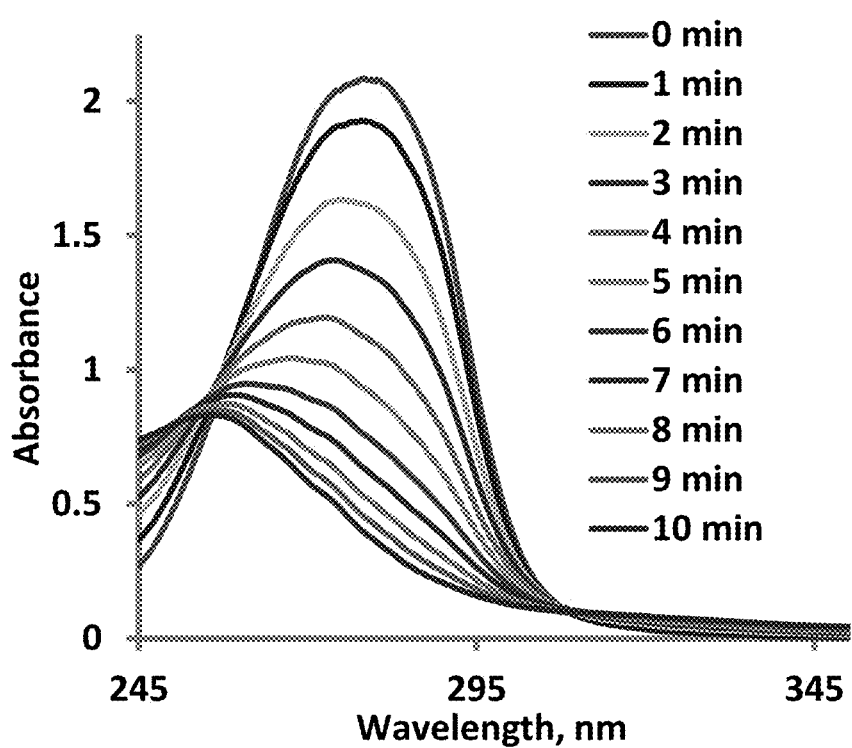
FIG. 2 is a graph of gel permeation chromatograph (GPC) traces of irradiated samples of the homopolymer 15 showing showing the change absorbance in λmax with an increase in photodegradation of the polymer.

In some embodiments, the present invention provides substituted phenacyl molecules and methods for making them. In other embodiments, the present invention provides photoresponsive polymers and copolymers wherein substituted phenacyl molecules are incorporated therein, and further provides methods of making them. In some embodiments of photoresponsive polymers/copolymers, the substituted phenacyl molecule is incorporated into the polymer/copolymer backbone. In such embodiments, photoirradiation of the polymer/copolymer will cause the substituted phenacyl group to break down, thus causing the polymer/copolymer to undergo degradation. In other embodiments of photoresponsive polymers/copolymers, the substituted phenacyl molecules extend as a side chain from the polymer/copolymer backbone. In yet other embodiments the substituted phenacyl molecules extend as a side chain from the polymer/copolymer backbone, and a drug or polymer additive is linked to the photoresponsive substituted phenacyl group such that photoirradiation releases the drug or additive. In yet other embodiments the substituted phenacyl molecules extend as a side chain from the polymer/copolymer backbone, and serve to link the polymer/copolymer to another polymer/copolymer backbone (i.e., serving as a crosslinking entity), and photoirradiation breaks the links.

In one embodiment, the present invention provides a novel substituted phenacyl composition of matter, particularly a substituted phenacyl molecule that can be employed to create molecules and polymers that exhibit photoresponsiveness. This novel composition is provided below as structure (I):

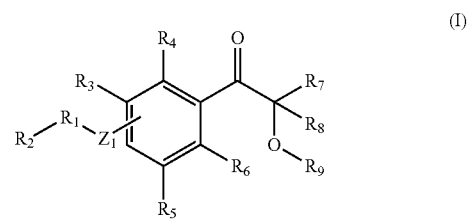

(I)

wherein $R_1$ is an alkyl chain of from C1 to C10; $R_2$ is a group of atoms containing at least one functional group; $R_3$, $R_4$, $R_5$, $R_6$, $R_7$, $R_8$ and $R_9$ are selected from any atom or group of atoms, and $Z_1$ is selected from O, S, HNC=O or $R_{10}$NC=O, wherein $R_{10}$ is selected from any atom or group of atoms. As indicated by the notation used, the $Z_1$ group may be at the ortho-, meta- or para-position, and it will be appreciated that the R groups at the ortho or meta position would, depending upon the position taken by the $Z_1$ groups, take up the para position that is shown without an R group in structure (I). In some embodiments, the $R_2$ and $R_9$ groups are selected to participate in homopolymerization or copolymerization. In some embodiments, $R_2$ is selected from a carboxyl group, a hydroxyl group and a vinyl group. In other embodiments, R9 is selected from a hydroxyl group and a vinyl group. In other embodiments, both $R_2$ and $R_9$ are selected from a hydroxyl group and a vinyl group. In other embodiments, both $R_2$ and $R_9$ are hydroxyl groups.

In particular embodiments, $R_3$ through $R_9$ are selected from H, Cl, Br, F, alkyl, vinyl, alkynyl, aryl, or alkoxy groups, and $R_1$, $R_2$, and $Z_1$ are selected as above. In other embodiments, $R_3$ through $R_9$ are selected from H, Cl, Br, F, alkyl, vinyl, alkynyl, aryl, or alkoxy groups, $R_1$ is an alkyl chain of from C1 to C10; $R_2$ is as above, and $Z_1$ is oxygen. In yet other embodiments, $R_3$ through $R_8$ are hydrogen, $R_9$ is any atom or group of atoms, $R_1$ is an alkyl chain of from C1 to C10, and $Z_1$ is oxygen. In a particular embodiment, $R_2$ is a hydroxyl group, $R_3$ through $R_9$ are hydrogen, $R_1$ is an alkyl chain of from C1 to C10, $Z_1$ is oxygen and is at the para position; and, in yet another particular embodiment, $R_2$ is a hydroxyl group, $R_3$ through $R_9$ are hydrogen, $R_1$ is a propylene chain (C3H6), $Z_1$ is oxygen and is at the para position such that the photoresponsive molecule has the following structure (II), herein named 2-hydroxy-1-(4-(3-hydroxypropoxy)phenyl)ethanone:

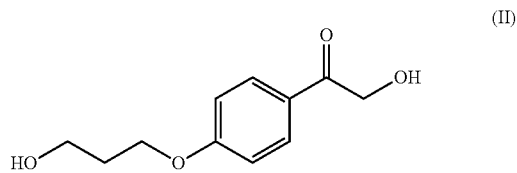 [SMILES: O=C(CO)c1ccc(OCCCO)cc1]

(II)

When employed to create a polymer or copolymer in accordance with this invention, the alkyl chain at $R_1$ renders the polymers/copolymers more soluble in common solvents, thus improving the processability of the polymers/copolymers.

In other embodiments, $R_2$ through $R_9$ are selected from H, Cl, Br, F, alkyl, vinyl, alkynyl, aryl, or alkoxy groups, $R_1$ is an alkyl chain of from C1 to C10, $R_2$ is —COOH, and $Z_1$ is oxygen. In a particular embodiment, $R_3$ through $R_9$ are hydrogen, $R_1$ is $CH_2$, $R_2$ is —COOH and $Z_1$ is oxygen.

The molecules taught above may be modified at $R_9$ to provide photoresponsive properties. This may be achieved by modifying the molecule or by employing the molecule in homo- or copolymerization, thus providing the needed $R_9$ group that contributes to the photoresponsive property. This will be described more fully below.

When photoirradiated, the substituted phenacyl molecules of this invention, whether alone or incorporated into a polymer, and with suitable O—$R_9$ substitution, cleave between the oxygen and the 2 position carbon of the phenacyl group, as generally represented in exemplary structures annotated below:

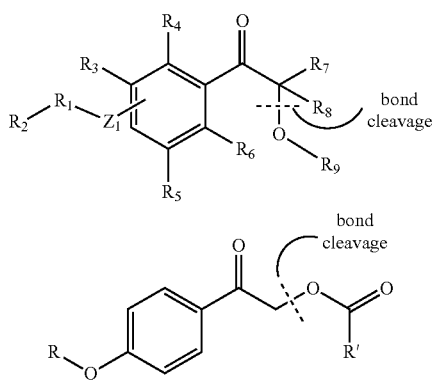

Suitable O—$R_9$ substitution would provide chemical groups that are leaving groups. In some embodiments the $R_9$ bound to the oxygen is selected from RC=O, wherein R represents any substitution. In other embodiments O—$R_9$ is selected from an ester group, a carbonate group, a phosphate group, a sulfate group and a sulfinate group. As will be shown more fully below, this bond cleavage is taken advantage of to provide photoresponsive molecules and polymers/copolymers.

In some embodiments, the present invention provides photoresponsive polymers and copolymers that include substituted phenacyl molecules in the backbone of the polymer/copolymer. The substituted phenacyl molecules are based on those disclosed above in structure (I). In particular embodiments, the polymers are polycarbonates. In other embodiments, the polymers are polyesters. In other embodiments, the polymers are copolmers.

Thus, in some embodiments, the present invention provides a composition of matter selected from a polymer, macromolecule, copolymer, oligmer, dendrimer, dendron, and macrocycle, the composition including the following molecular unit represented by structure (III):

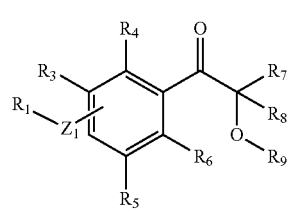

wherein $R_1$ is alkyl chain of from C1 to C10; $R_3$, $R_4$, $R_5$, $R_6$, $R_7$ and $R_8$ may be any atom or group of atoms; $Z_1$ is selected from O, S, HNC=O or $R_{10}$NC=O, wherein $R_{10}$ is selected from any atom or group of atoms, and O—$R_9$ is a leaving group. In some embodiments the $R_9$ bound to the oxygen is selected from RC=O, wherein R represents any substitution. In other embodiments O—$R_9$ is selected from an ester group, a carbonate group, a phosphate group, a sulfate group and sulfinate group. As indicated by the notation used, the $Z_1$ group may be at the ortho, meta or para position, and it will be appreciated that the R groups at the ortho or meta position would, as the case may be, take up the para position that is shown without an R group in structure (III). In particular embodiments, $R_3$ through $R_8$ are hydrogen, and $Z_1$ is oxygen and is at the para position. In other embodiments O—$R_9$ is selected from an ester group, a carbonate group, a phosphate group, a sulfate group and sulfinate group, and $R_3$ through $R_8$ are hydrogen, and $Z_1$ is oxygen and is at the para position.

In some embodiments, the polymer is a polycarbonate homopolymer having the following structure (IV):

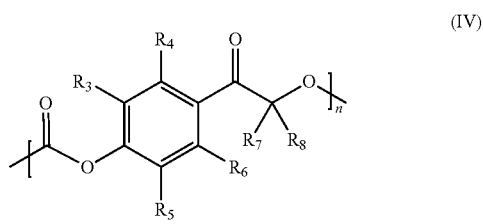

wherein $R_3$, $R_4$, $R_5$, $R_6$, $R_7$, and $R_8$ may be any atom or group of atoms and n is any number of repeating units. In particular embodiments, $R_3$-$R_8$ are hydrogen. In particular embodiments, n is four or more.

In some embodiments, the polymer is a polycarbonate copolymer having the following structure (V):

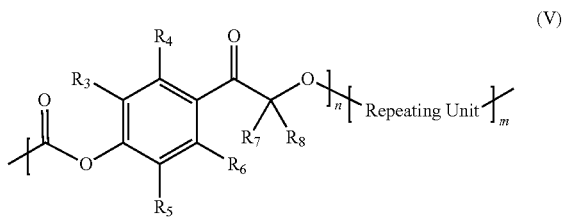

wherein $R_3$, $R_4$, $R_5$, $R_6$, $R_7$, and $R_8$ may be any atom or group of atoms, n is any number of repeating units for the substituted phenacyl photoresponsive unit, "Repeating Unit" represents the repeating unit contributed by a comonomer or copolymer, m represents any number of repeating units of the "Repeating Unit". The n and m repeating units are in statistical arrangement. In particular embodiments, $R_3$-$R_8$ are hydrogen.

The comonomer can be virtually any monomer using suitable reagents and reaction conditions to copolymerize with the photoresponsive molecule employed in the polymerization. In some embodiments, the comonomer that contributes the "Repeating Unit" is ethylene glycol. In some embodiments, the "Repeating Unit" is contributed by a copolymer selected from poly(ethylene glycol) and polycaprolatone.

In some embodiments, the comonomer is ethylene glycol, and the copolymer has the following structure (VI):

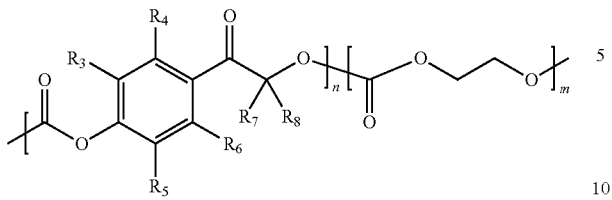

(VI)

wherein $R_3$, $R_4$, $R_5$, $R_6$, $R_7$, and $R_8$ may be any atom or group of atoms, and n and m represent the number of each repeating unit. In particular embodiments, $R_3$-$R_8$ are hydrogen.

In other embodiments, the copolymer poly(ethylene glycol) is employed, and the copolymer has the following structure (VII):

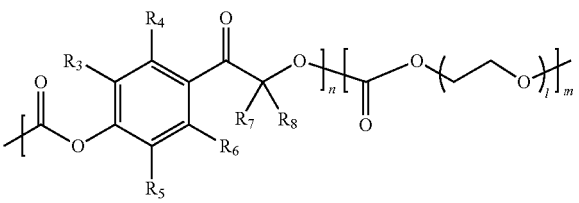

(VII)

wherein $R_3$, $R_4$, $R_5$, $R_6$, $R_7$, and $R_8$ may be any atom or group of atoms, and n, m and l represent the number of each repeating unit. In particular embodiments, $R_3$-$R_8$ are hydrogen.

In some embodiments, the polymer is a polycarbonate homopolymer having the following structure (VIII):

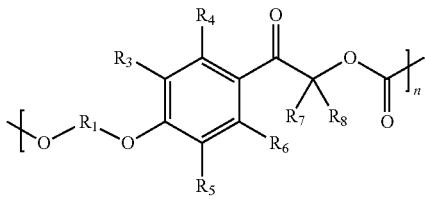

(VIII)

wherein $R_3$, $R_4$, $R_5$, $R_6$, $R_7$, and $R_8$ may be any atom or group of atoms, $R_1$ is an alkyl chain of from C1 to C10, and n represents the number of repeating units. In particular embodiments, $R_3$-$R_8$ are hydrogen and $R_1$ is a propylene chain ($C_3H_6$). In particular embodiments, n is four or more.

In some embodiments, the polymer is a polycarbonate copolymer having the following structure (IX):

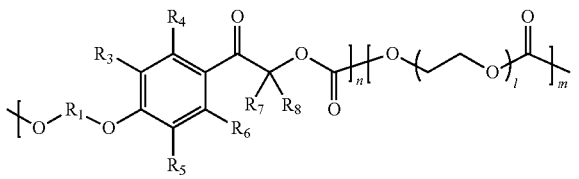

(IX)

wherein $R_3$, $R_4$, $R_5$, $R_6$, $R_7$, and $R_8$ may be any atom or group of atoms, and n, m and l represent the number of each repeating unit. In some embodiments, the ratio of n to m units may range from 1:100 to 100:1, and in other embodiments, from 10:100 to 100:10. In particular embodiments, $R_3$-$R_8$ are hydrogen and $R_1$ is a propylene chain ($C_3H_6$).

In some embodiments, the polymer is a polyester homopolymer having the following structure (X):

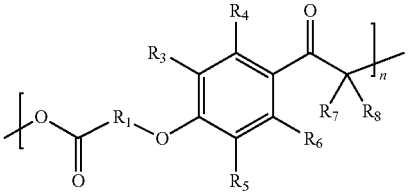

(X)

wherein $R_3$, $R_4$, $R_5$, $R_6$, $R_7$, and $R_8$ may be any atom or group of atoms, $R_1$ is an alkyl chain of from C1 to C10, and n represents the number of repeating units. In particular embodiments, $R_3$-$R_8$ are hydrogen and $R_1$ is a methylene ($CH_2$) group.

In other embodiments, the polymer is a polyester homopolymer having the following structure (XI):

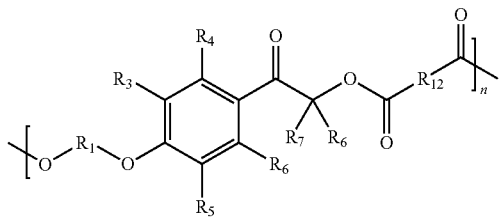

(XI)

wherein $R_3$, $R_4$, $R_5$, $R_6$, $R_7$, and $R_8$ may be any atom or group of atoms, $R_1$ is an alkyl chain of from C1 to C10, $R_{12}$ is either a bond between the two carbonyl groups or is an alkyl chain of from C1 to C10, and n represents the number of repeating units. In particular embodiments, $R_3$-$R_8$ are hydrogen, $R_1$ is a propylene chain ($C_3H_6$) and $R_{12}$ is a butylene chain ($C_4H_8$).

In other embodiments, the present invention provides photoresponsive polymers and copolymers that include substituted phenacyl molecules extending in side chains off of the backbone of a polymer/copolymer. The substituted phenacyl molecules are based on those disclosed above in structure (I); however, in other embodiments, the substituted phenacyl molecules extending from the polymer backbone are not so limited, and do not include the $R_1$ group represented in (I). In particular embodiments, the polymers are polyacrylates. In other embodiments, the polymers are polyacrylamides. In other embodiments, the polymers are polymethacrylate. In other embodiments, the polymers include copolymers.

A general structure (XII) is provided below to help disclose the concept of incorporating the substituted phenacyl molecule as a side chain off of a polymer backbone:

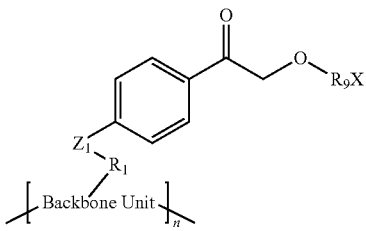

(XII)

wherein $R_1$ is alkyl chain of from C1 to C10, $Z_1$ is selected from O, S, HNC=O or $R_{10}$NC=O, wherein $R_{10}$ is selected from any atom or group of atoms, O—$R_9$ forms a part of a the drug or additive, and X represents a drug or additive or portion of a drug or additive. In some embodiments the O—$R_9$X group is O—CX=O. bound to the oxygen is selected from C=O. In other embodiments O—$R_9$X is selected from a drug or additive providing at O—$R_9$ an ester group, a carbonate group, a phosphate group, a sulfate group and a sulfinate group.

By providing the O—$R_9$X groups as above, the drug or additive can be incorporated to extend as part of a side chain off of a polymer, and the drug or additive can be released upon irradiation, with the unit cleaving to release the O—$R_9$X group.

This concept can also be applied to de-crosslink a crosslinked polymer network. First, a crosslinked polymer network is formed according to the general structure (XIII) below:

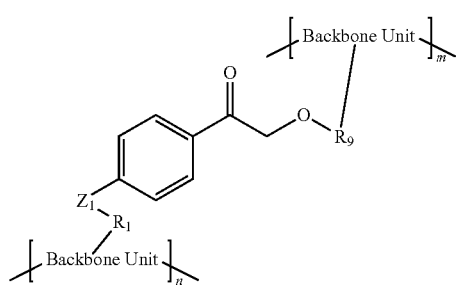

(XIII)

Wherein $R_1$ and $R_9$ are selected from a group of atoms that link the photoresponsive unit to the polymer backbone; and $Z_1$ is selected from O, S, HNC=O or $R_{10}$NC=O, wherein $R_{10}$ is selected from any atom or group of atoms. It will be appreciated that the substituted phenacyl thus links polymer backbones and serves as a crosslinker. Upon irradiation, the linking unit will cleave and the polymer matrix will be de-crosslinked. In some embodiments the $R_9$ bound to the oxygen is selected from RC=O, wherein R represents any substitution. In other embodiments O—$R_9$ is selected from an ester group, a carbonate group, a phosphate group, a sulfate group and a sulfinate group.

When $Z_1$ is oxygen or sulfur, the photoresponsive molecule of structure (I) can be made according to the following reaction scheme (Scheme 1):

SCHEME 1

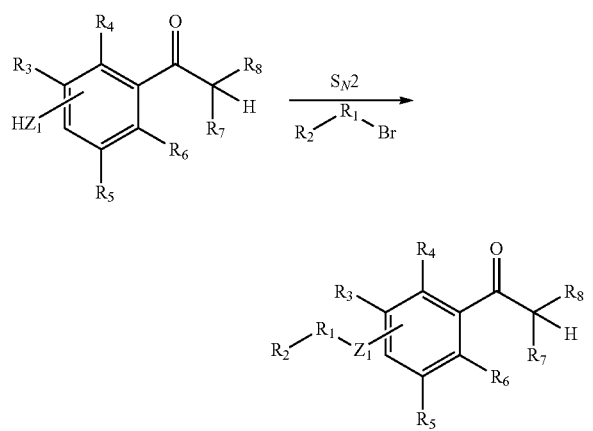

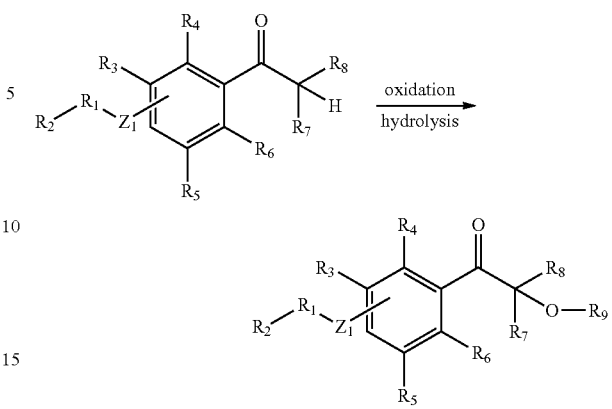

wherein $R_1$ is an alkyl chain of from C1 to C10; $R_2$ is a group of atoms containing at least one functional group or protected functional group that does not affect the desired reaction; $R_3$, $R_4$, $R_5$, $R_6$, $R_7$, and $R_8$ may be any atom or group of atoms; $R_9$ is hydrogen; $Z_1$ is O or S. The starting phenacyl molecule can be purchased. The chain extension $R_1$ and the functional group $R_2$ are added by reacting the starting phenacyl molecule with a functionalized alkyl halide, $R_2$—$R_1$-Halide, wherein $R_2$ is a group of atoms containing at least one functional group or protected functional group that does not affect the reaction of this step. These react through a bimolecular nucleophilic substitution ($S_N2$). This reaction is followed by oxidation of the H at the 2 position of the phenacyl molecule, and then hydrolysis to provide a hydroxyl group. Using generally chemistry knowledge, further modification could be applied to get the desired substitution, especially for $R_2$ and $R_9$.

When $Z_1$ is NH or $NR_{10}$, the photoresponsive molecule of structure (I) can be made according to the following reaction scheme (Scheme 2):

SCHEME 2

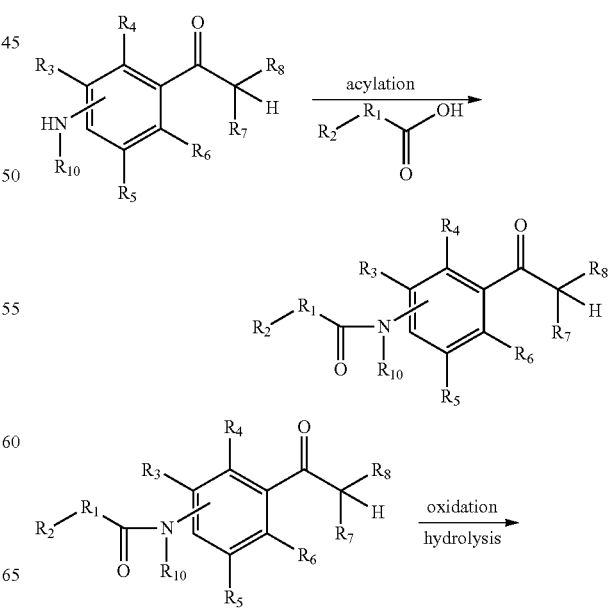

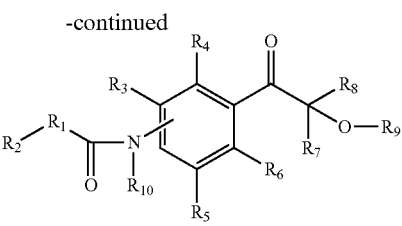

wherein $R_1$ is an alkyl chain of from C1 to C10; $R_2$ is a group of atoms containing at least one functional group or protected functional group that does not affect the desired reaction; $R_3$, $R_4$, $R_5$, $R_6$, $R_7$, and $R_8$ may be any atom or group of atoms; $R_9$ is hydrogen. The starting phenacyl molecule can be purchased. The chain extension $R_1$ and the functional group $R_2$ are added by acylation of the amine with a functionalized acylating agent, for example, a carboxylic acid, $R_2$—$R_1$—COOH, wherein $R_2$ is a group of atoms containing at least one functional group or protected functional group that does not affect the reaction of this step. This reaction is followed by hydrolysis to provide the hydroxyl group. Using generally chemistry knowledge, further modification could be applied to get the desired substitution, especially for $R_2$ and $R_9$.

Specific molecules are shown in the examples section below.

The substituted phenacyl molecules bearing suitable functional groups can be polymerized (or copolymerized with other monomers) through general polymer chemistry knowledge, such as by employing step-growth polymerization techniques. For example, hydroxyl groups can react with triphosgene to make polycarbonates or can react with acid groups to form polyesters. Specific polymerizations are shown in the examples section below.

Similarly, the substituted phenacyl molecules bearing suitable functional groups can be secured to polymer backbones and can bear additives or drugs through general polymer chemistry knowledge, such as by acylation of the hydroxyl group when $R_9$ is H. The substituted phenacyl molecules may also be employed to crosslink polymers through the selection of suitable functional groups and general polymer chemistry. For example, when $R_2$ and $R_9$ both have at least one vinyl group that can be polymerized together with other vinyl compound. Specific polymerizations are shown in the examples section below.

Disposable plastic products are a necessary part of modern life, but their toll on the environmental is significant because they do not readily degrade. By formulating such plastic products from polymers that incorporate the photoresponsive molecules taught herein in the backbone, the products could be made to degrade upon exposure to light.

Polymer matrices are used for delivery of therapeutics since such systems provide sustained delivery of the therapeutic over a long time period (as in an implant) or in transdermal delivery (eg. nicotine patch). Also polymer-drug conjugates are increasingly used for site specific delivery of therapeutics. The proposed materials have a potential future in dermal patches or in polymer-drug conjugates wherein therapeutic delivery is achieved only upon irradiation of the polymer. This type of photoresponsive material has potential applications in ocular drug delivery applications In such applications, the polymer matrix can be degraded by ambient sunlight entering the eye to release the encapsulated drug.

There is an increasing need for developing materials with micron and sub-micron sized features. Photoresists with micron sized features are made using materials that efficiently degrade under UV irradiation. Materials used in the microprocessor industry for such applications either contain an additive that makes the polymer more soluble after irradiation (Novalak resin) or become soluble upon irradiation due to deprotection of the phenol side chain. The polymers proposed here could find use in such applications since they undergo backbone cleavage under mild irradiation conditions.

Alternatively, recent tissue engineering research has shown that cellular functions such as adhesion and motility can be controlled by patterned materials with micron sized features. For example, physical guidance of astrocyte adhesion and proliferation along micro-patterned polystyrene was demonstrated. Since the proposed polymers would be photodegradable they can be used to fabricate micron and sub-micron featured surfaces for studies of cell-material interactions. Additionally, due to the more efficient photoactive materials proposed here, 3-D structures of these materials such as scaffolds with well aligned channels for nerve guidance could be fabricated as shown in FIG. 1.

Polycarbonates and polyesters of these polymers have been synthesized. Most of the current studies have been carried out on the polycarbonates. However, both the polycarbonates and polyesters undergo photoinitiated degradation of the backbone. The polycarbonates are synthesized by the polymerization of alkoxyphenacyl based diols using triphosgene. Poly(ethylene glycol) or polycaprolactone diol can also be incorporated as a monomer to modulate the properties of the polymer. For the synthesis of the polyesters, the alkoxyphenacyl diols are reacted with diacids in the presence of a coupling agent such as diisopropylcarbodiimide. All these synthetic procedures are detailed in the examples.

In light of the foregoing, it should be appreciated that the present invention significantly advances the art by providing photoresponsive molecules and photoresponsive polymers that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Materials and Equipment

Sodium hydroxide, sodium bisulfate, potassium carbonate, 18-crown-6, p-toluene sulfonic acid, N,N-dimethylformamide (extra dry), dichloromethane (extra dry), 4 Å molecular sieves, 3-bromo-1-propanol, and triphosgene were purchased from Fisher and used as received. Sodium hydroxide, sodium sulfate, sodium acetate trihydrate, cupric bromide, and 4-hydroxyacetophenone were purchased from Acros Organics and used as received. Poly(ethylene glycol) was purchased from Sigma Aldrich. Acetone was dried over activated 4 Å molecular sieves. Pyridine was dried over potassium hydroxide. Other chemicals are also purchased from commercial source and used as received unless otherwise specificated in the procedure.

1H NMR was recorded on a Varian Mercury 300 MHz or Varian 500 MHz NMR spectrometer. 13C NMR was recorded on a Varian 500 MHz NMR spectrometer (125 MHz for carbon). Polymer molecular weights were analyzed on a TOSOH EcoSEC HLC-8320 GPC, with two TSK-GEL™ Super H 3000 columns and one TSK-GEL™ Super H 4000 column in series, using $CHCl_3$ as the mobile phase. Irradiation was carried on in Rayonet™ RPR-200 reactor at 300 nm (5.34 mW/cm2). The intensity of the irradiation was measured by an OPHIR AN/2 light power meter. IR was recorded on a SHIMADZU MIRacle 10 ATR-FTIR. UV was recorded on a SHIMADZU UV-1800 UV spectrophotometer. Fluorescence was measured on BioTek Synergy Mx MultiMode Microplate Reader. AFM was obtained on DI MultiMode SPM AFM. ESI and MALDI were characterized at The University of Akron Mass Spectrometry Center. SEM and Tensile modulus was measured in the Applied Polymer Research Center at The University of Akron.

Photoresponsive Molecules

I. Synthesis of 2-hydroxy-1-(4-hydroxyphenyl)ethanone

A. Synthesis of (2-Bromo-1-(4-hydroxyphenyl)ethanone)

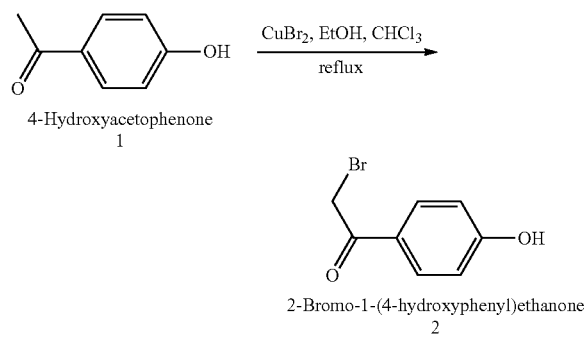

A solution of 4-hydroxyacetophenone (9.0 g, 66.1 mmol) in CHCl3 (70 ml) was added to a suspension of cupric bromide (29.5 g, 132.2 mmol, 2eq), in ethanol (50 ml). The mixture was vigorously stirred and refluxed for 3.5 hours. Over the course of the reaction, the black $CuBr_2$ turned to white CuBr. The reaction mixture (dark green) was filtered, and the solvent was removed to give a violet solid. The solid was dispersed between water and ethyl acetate to give a green water phase and light green/light yellow ethyl acetate phase, with white solid suspension occasionally. The organic layer was dried over sodium sulfate and solvent was removed to give a dark green or purple solid. Further purification can be performed by column chromatography (25-75, ethyl acetate-hexane) to give the product as a white solid (14.1 g 99.3% yield): 1H NMR (500 MHz, DMSO-d6) δ 4.77 (s, 2H), 6.87 (d, J=8.80 Hz, 2H), 7.88 (d, J=8.80 Hz, 2H), 10.49 (s, 1H). 13C NMR (125 MHz, DMSO-d6) δ 33.3 (s), 115.3 (s), 125.3 (s), 131.4 (s), 162.6 (s), 189.8 (s); MS (ESI) m/z calc for $C_8H_8BrO_2$ [MH]+ 215.0, found 214.7.

B. Synthesis of (2-(Acetyloxy)-1-(4-hydroxyphenyl)-ethanone)

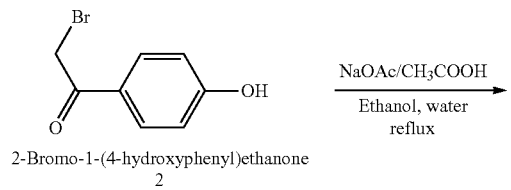

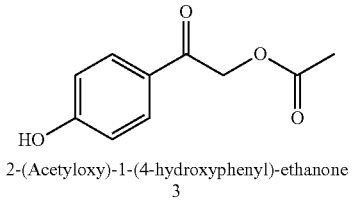

2-(Acetyloxy)-1-(4-hydroxyphenyl)-ethanone
3

A solution of 2 (14.2 g, 66.0 mmol) in 100 ml ethanol was added to a solution of sodium acetate trihydrate (17.9 g, 132 mmol, 2 eq) in 50 ml water. Acetic acid (6.6 ml) was then added to the above mixture. The mixture was stirred and refluxed for 3.5 hours. After most of the solvent was removed on a rotary evaporator, additional water was added to make a total volume of around 60 ml. The product was extracted with ethyl acetate (60 ml each time, 3×). The organic layers were combined and dried over sodium sulfate. The solvent was removed on a rotary evaporator to give the crude product as a light yellow solid), which was purified by column chromatography (30% ethyl acetate-70% hexane). The product was obtained as a white powder (6.35 g, 49.5% yield): mp 137-139° C.; 1H NMR (500 MHz, DMSO-d6) δ 2.13 (s, 3H), 5.36 (s, 2H), 6.88 (d, J=8.78 Hz, 2H), 7.84 (d, J=8.78 Hz, 2H), 10.51 (s, 1H); 13C NMR (125 MHz, DMSO-d6) δ 20.85 (s), 66.41 (s), 115.9 (s), 125.9 (s), 130.7 (s), 163.1 (s), 170.3 (s), 191.1 (s); MS (ESI) m/z calc for $C_{10}H_{10}NaO_4$ [MNa]+ 217.0, found 217.0.

C. (2-Hydroxy-1-(4-hydroxyphenyl)ethanone)

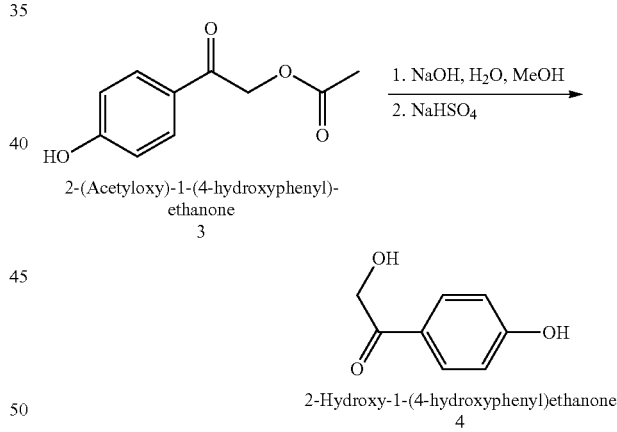

A solution of sodium hydroxide (2.61 g, 65.4 mmol) in 26 ml water was added to a solution of 3 (6.35 g, 32.7 mmol) in 78 ml methanol. The mixture was stirred at room temperature for 1 hour, during which time the reaction mixture turned yellow. Then sodium bisulfate (3.9 g, 32.7 mmol) was used to neutralize the sodium hydroxide. Methanol was removed on a rotary evaporator, giving a suspension of white particles in water. Additional water was added to make a total volume of around 60 ml, which was extracted with ethyl acetate (60 ml each time, 3×). The organic layers were combined and dried over sodium sulfate. The solvent was removed to give a crude product as a yellow solid or viscous liquid. Further purification was performed by column chromatography eluenting with 35% ethyl acetate –65% hexane to give the product as a white powder (2.4 g, 15.7 mmol, 48.3% yield): mp 174-179°

C.; 1H NMR (500 MHz, DMSO-d6) δ 4.68 (d, J=5.62 Hz, 2H), 4.84 (t, J=5.62 Hz, 1H) 6.84 (d, J=8.80 Hz, 2H), 7.81 (d, J=8.78 Hz, 2H), 10.34 (s, 1H); 13C NMR (125 MHz, DMSO-d6) δ 65.2 (s), 115.8 (s), 126.5 (s), 130.5 (s), 162.7 (s), 197.6 (s); MS (ESI) m/z calc for $C_8H_8NaO_3$ [MNa]+ 175.0, found 174.9.

II. Synthesis of 2-Hydroxy-1-((4-(3-hydroxypropoxy)phenyl)ethanone

A. Synthesis of (1-(4-(3-Hydroxypropoxy)phenyl)ethanone)

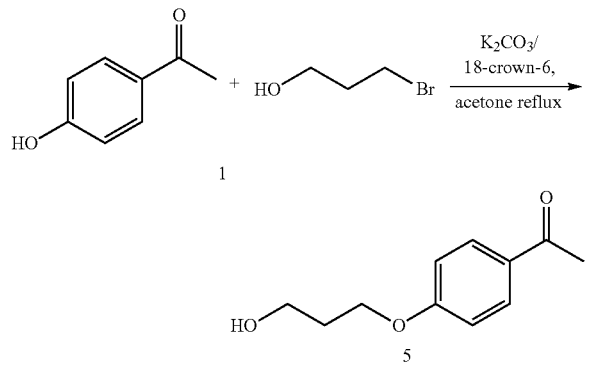

4-hydroxyacetophenone (10.0 g, 73.5 mmol), 18-crown-6 (0.2912 g, 1.1 mmol) and potassium carbonate (13.2 g, 95.5 mmol) were taken in a two neck round bottom flask equipped with a stir bar. The flask was vacuumed and refilled with $N_2$ three times. Acetone (22 mL) was added through syringe and needle. The mixture was stirred at room temperature for 30 minutes, followed by addition of 1-bromo-3-propanol (7.8 mL, 88.1 mmol). The mixture was refluxed for 24 hours and then filtered. Acetone was removed under vacuum to yield the crude product (15.0 g) which was used in the next step without purification. Purification can be performed by column chromatography (30% ethyl acetate and 70% hexane): mp 37-41° C.; 1H NMR (500 MHz, DMSO-d6) δ 1.86-1.91 (m, 2H), 2.50 (s, 3H, overlap with DMSO), 3.56 (m, 2H), 4.13 (t, J=6.36 Hz, 2H), 4.55 (t, J=5.14 Hz, 1H), 7.03 (d, J=8.80 Hz, 2H), 7.92 (d, J=9.05 Hz, 2H); 13C NMR (125 MHz, DMSO-d6) δ 26.3 (s), 31.9 (s), 57.1 (s), 64.9(s), 114.1(s), 129.7 (s), 130.3 (d), 162.5 (s), 196.1 (s); IR (ATR) ν 3439, 2941, 1654, 1595, 1255, 1170, 1056, 948, 827 cm-1; MS (ESI) m/z calc for $C_{11}H_{14}NaO_3$ [MNa]+ 217.1, found 216.8. NMR results were consistent with the previously reported characterization in CDCl3.4

B. Synthesis of (2-Bromo-1-(4-(3-hydroxypropoxy)phenyl)ethanone)

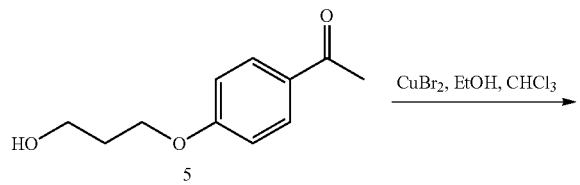

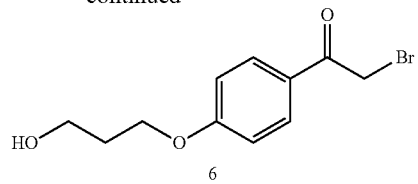

A solution of 5 (14.2 g, 73.5 mmol) in $CHCl_3$ (70 mL) was added to a suspension of cupric bromide (32.8 g, 146.9 mmol, 2eq), in ethanol (50 mL). The mixture was vigorously stirred and refluxed for 4 hours. Over the course of the reaction, the black $CuBr_2$ turned to white CuBr. The reaction mixture (dark green) was filtered, and the solvent was removed to give a violet solid. The solid was dispersed between water and ethyl acetate to give a green water phase and light green/light yellow ethyl acetate phase, with white solid suspension occasionally. The organic layer was dried over sodium sulfate and solvent was removed to give a dark green or purple solid. Further purification was performed by column chromatography (25% ethyl acetate-75% hexane) to give a pure product as a white solid (15.0 g, 54.9 mmol, 74.8% yield over two steps; mp 65-66° C.; 1H NMR (500 MHz, DMSO-d6) δ 1.86-1.91 (m, 2H), 3.56 (t, J=6.11 Hz, 2H), 4.15 (t, J=6.60 Hz, 2H), 4.5-4.6 (br s, 1H), 4.82 (s, 2H), 7.06 (d, J=8.80 Hz, 2H), 7.97 (d, J=8.80 Hz, 2H); 13C NMR (125 MHz, DMSO-d6) δ 31.8 (s), 33.45 (s), 57.0 (s), 65.0 (s), 114.4 (s), 126.5 (s), 131.1 (d), 163.0 (s), 190.0 (s); IR (ATR) ν 3429, 3361, 2953, 1678, 1313, 1292, 1118, 1958, 844, 694 cm-1; MS (ESI) m/z calc for $C_{11}H_{13}BrNaO_3$ [MNa]+ 295.0, found 294.6.

C. Synthesis of (2-(Acetyloxy)-1-(4-(3-hydroxypropoxy)phenyl)-ethanone)

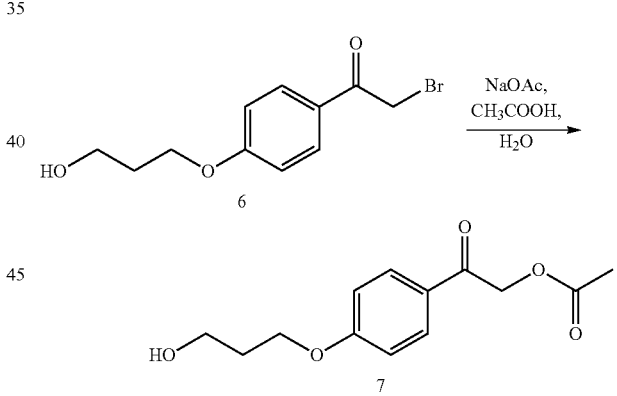

A solution of 6 (15.0 g, 54.9 mmol) in ethanol (110 mL) was added to a solution of sodium acetate trihydrate (15.0 g, 109.9 mmol, 2 eq) in 55 mL water. Acetic acid (5.5 mL) was then added to the above mixture. The mixture was stirred and refluxed for 3.5 hours. After most solvent was removed on a rotary evaporator, additional water was added to make a total volume of around 60 mL. The product was extracted with ethyl acetate (60 mL×3). The organic layers were combined and dried over sodium sulfate. The solvent was removed on a rotary evaporator to give the crude product as a light yellow solid (13.8 g, 54.7 mmol, 99.6% yield), which was directly used for the next step. Further purification can be performed by column chromatography (40% ethyl acetate-60% hexane): mp 71.5-72.5° C.; 1H NMR (500 MHz, DMSO-d6) δ 1.84-1.94 (m, 2H), 2.75 (s, 3H), 3.51-3.61 (m, 2H), 4.14 (t, J=6.60 Hz, 2H), 4.58 (t, J=5.14 Hz, 1H), 5.40 (s, 2H), 7.06 (d, J=8.80 Hz, 2H), 7.92 (d, J=8.80 Hz, 2H); 13C NMR (125 MHz, DMSO-d6) δ 20.3 (s), 31.8 (s), 57.0 (s), 65.0 (s), 66.0 (s), 114.4 (s), 126.5 (s), 130.0 (d), 163.0 (s), 169.8 (s), 190.9 (s); IR (ATR) v3483, 2941, 1737, 1666, 1600, 1255, 1220, 1176, 1078, 1060, 950, 802 cm-1; MS (ESI) m/z calc for $C_{13}H_{16}NaO_5$ [MNa]+ 275.1, found 274.8.

D. Synthesis of (2-Hydroxy-1-(4-(3-hydroxypropoxy)phenyl)ethanone)

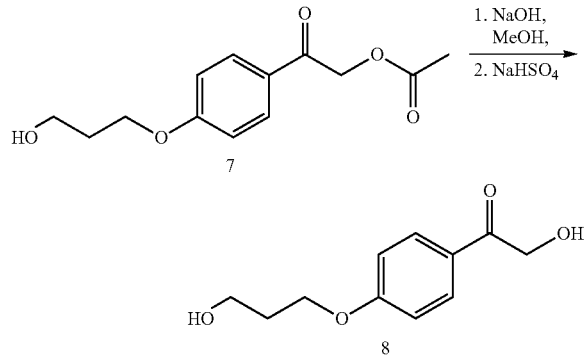

A solution of sodium hydroxide (2.62 g, 65.6 mmol) in 26 mL water was added to a solution of 7 (13.8 g, 54.7 mmol) in 80 mL methanol. The mixture was stirred at room temperature for 2 hours. Then sodium bisulfate (2.0 g, 16.4 mmol) was used to neutralize the sodium hydroxide. Methanol was removed on a rotary evaporator, giving a suspension of white particles in water. Additional water was added to make a total volume of around 60 mL, which was extracted with ethyl acetate (60 mL×3). The organic layers were combined and dried over sodium sulfate. The solvent was removed to give the crude product as a yellow solid or viscous liquid. Further purification was performed by column chromatography (50% ethyl acetate-50% hexane) to give the pure product as a white powder (5.3 g, 25.2 mmol, 46% yield): mp 100-101° C.; 1H NMR (500 MHz, DMSO-d6) δ 1.83-1.92 (m, 2H), 3.52-3.58 (m, 2H), 4.13 (t, J=6.36 Hz, 2H), 4.57 (t, J=5.14 Hz, 1H), 4.72 (d, J=5.87 Hz, 2H), 4.94 (t, J=5.87 Hz, 2H), 7.03 (d, J=8.80 Hz, 2H), 7.90 (d, J=8.80 Hz, 2H); 13C NMR (125 MHz, DMSO-d6) v 31.8 (s), 57.0 (s), 64.8 (d), 114.3 (s), 127.1 (s), 129.8 (d), 162.6 (s), 197.3 (s); IR (ATR) v3417, 3352, 1605, 1576, 1514, 1423, 1404, 1306, 1111, 1101, 1040, 982, 945 cm-1; MS (ESI) m/z calc for $C_{11}H_{14}NaO_4$ [MNa]+ 233.1, found 232.8.

III. Synthesis of (2-(4-(2-Hydroxyacetyl)phenoxy)acetic acid)

A. Synthesis of (Acetic acid, 2-[4-[2-(acetyloxy)acetyl]phenoxy]-, methyl ester)

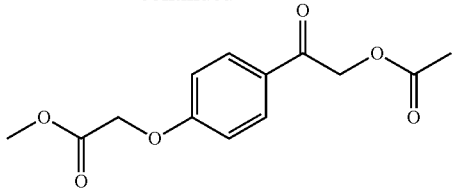

Acetic acid, 2-[4-[2-(acetyloxy)acetyl]phenoxy]-, methyl ester

9

3 (2.4 g, 12.9 mmol) and potassium carbonate (2.2 g, 16.1 mmol, 1.25 eq) were added into a two neck flask equipped with a stir bar. The flask was vacuumed and refilled with $N_2$ three times. Then anhydrous acetone (20 ml) was added and the mixture was stirred for 30 minutes before methyl bromoacetate (1.35 ml, 2.16 g, 14.2 mmol, 1.1 eq) was added. The reaction mixture was refluxed for 3 hours and filtered. The solvent was removed on a rotary evaporator to give the crude product as a light yellow solid. Further purification by column chromatography (30% ethyl acetate-70% hexane) gave the product as a white solid (3.0 g, 88.2% yield): 1H NMR (300 MHz, DMSO-d6) δ 2.14 (s, 3H), 3.71 (s, 3H), 4.95 (s, 2H), 5.41 (s, 2H), 7.07 (d, J=9.08 Hz, 2H), 7.91 (d, J=9.08 Hz, 2H).

B. Synthesis of (2-(4-(2-Hydroxyacetyl)phenoxy)acetic acid)

9 (1.95 g, 7.3 mmol) and p-Toluenesulfonic acid (PTSA) (0.27 g, 1.5 mmol) were dissolved in a mixture of 60 ml acetonitrile and 60 ml water. The solution was stirred and refluxed for 24 hours, following which acetonitrile was removed on a rotary evaporator. The product was extracted with ethyl acetate. The organic layers were combined, and dried over sodium sulfate. Solvent was removed and the crude product was obtained as a yellow powder which was purified by re-crystallization from ethyl acetate-hexane to give the pure product as a white powder (0.3 g, 19.5% yield): 1H NMR (500 MHz, DMSO-d6) δ 4.73 (s, 2H), 4.76 (s, 2H), 4.96 (s, 1H), 7.01 (d, J=8.20 Hz, 2H), 7.90 (d, J=8.20 Hz, 2H); 13C NMR (125 MHz, DMSO-d6) δ 65. (s), 65.5 (s), 114.9 (s), 128.3 (s), 130.2 (s), 162.2 (s), 170.1 (s), 197.9 (s); IR (ATR) v3370, 2923, 2655, 1705, 1670, 1599, 1254, 1182, 1092, 1074, 986, 835 cm-1.F

IV. Synthesis of (Methyl 2-(4-(2-hydroxyacetyl)phenoxy)acetate)

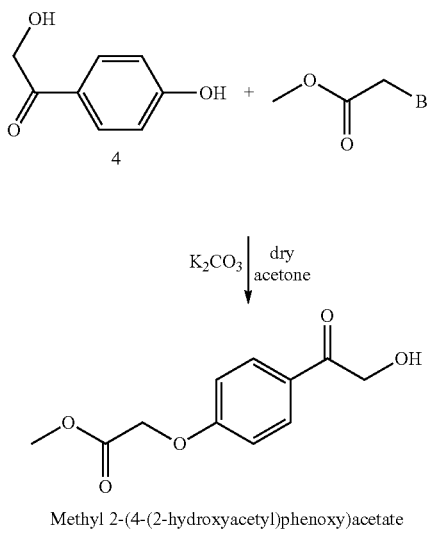

Methyl 2-(4-(2-hydroxyacetyl)phenoxy)acetate
11

4 (0.5 g, 3.3 mmol) and potassium carbonate (0.57 g, 4.1 mmol, 1.25 eq) were put in a two neck flask equipped with a stir bar. The flask was vacuumed and refilled with $N_2$ for three times. Then anhydrous acetone (20 ml) was added and the mixture was stirred for 30 minutes before methyl bromoacetate (0.34 ml, 0.55 g, 3.6 mmol, 1.1 eq) was added. The reaction mixture was refluxed for 3 hours and filtered. The solvent was removed on a rotary evaporator to give the crude product as a light yellow solid. Further purification by column chromatography (35% ethyl acetate –65% hexane) gave the pure product as a white solid (0.53 g, 71.9% yield): 1H NMR (300 MHz, DMSO-d6) δ 3.71 (s, 3H), 4.73 (d, J=5.86 Hz, 2H), 4.91 (s, 2H), 4.95 (s, 1H), 7.04 (d, J=8.20 Hz, 2H), 7.90 (d, J=8.20 Hz, 2H).

V. Synthesis of 1-(4-(3-hydroxypropoxy)-3,5-dimethoxyphenyl)ethanone (Example of R3-R8 Substitution)

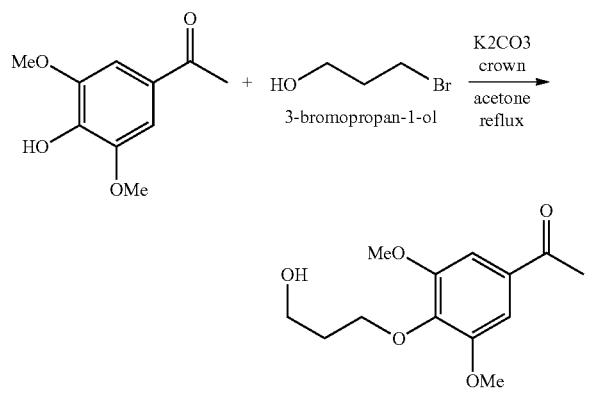

1-(4-hydroxy-3,5-dimethoxyphenyl)ethanone (3.0 g, 15.3 mmol), 18-crown-6 (0.0606 g, 0.229 mmol) and potassium carbonate (2.74 g, 19.9 mmol) were taken in a two neck round bottom flask equipped with a stir bar. The flask was vacuumed and refilled with N2 three times. Acetone (30 mL) was added through syringe and needle. The mixture was stirred at room temperature for 30 minutes, followed by addition of 1-bromo-3-propanol (1.6 mL, 18.3 mmol). The mixture was refluxed for 24 hours and then filtered. Acetone was removed under vacuum to yield the crude product (3.8 g) which was used in the next step without purification. Purification can be performed by column chromatography (30% ethyl acetate and 70% hexane) to get pure product (1.64 g): 1H NMR (300 MHz, DMSO-d6) δ ppm 1.76 (t, J=6.44 Hz, 2H) 2.55 (s, 3H) 3.54 (d, J=5.27 Hz, 2 H) 3.82 (s, 6 H) 4.01 (q, J=7.03 Hz, 2 H) 7.22 (s, 2 H).

Photoresponsive Polycarbonate Polymers

I. Synthesis of Poly(2-(acetyloxy)-1-(4-hydroxyphenyl)-ethanone carbonate)

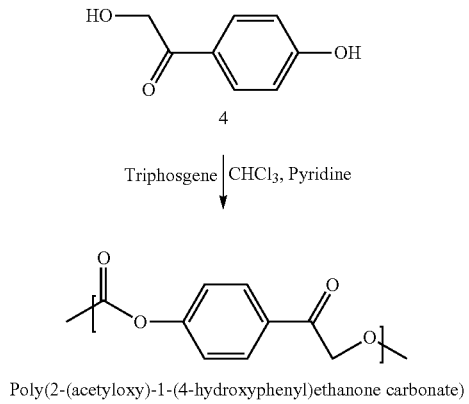

Poly(2-(acetyloxy)-1-(4-hydroxyphenyl)ethanone carbonate)
12

4 (1 g, 6.6 mmol) was added to a two neck flask equipped with a stir bar. The flask was vacuumed and refilled with $N_2$ three times. Chloroform (5 ml) and pyridine (1.8 ml) were added. Then the solution was stirred and cooled with ice bath. In a small vial, triphosgene (0.68 g, 2.3 mmol) was dissolved in 5 ml chloroform. The triphosgene solution was added dropwise to the reaction mixture and almost immediately solid material started to precipitate. The reaction was allowed to proceed for 2 hours, by the end of which the reaction temperature warmed up to room temperature. Then the polymer was precipitated in cold isopropanol (200 ml) and was obtained as a white solid. The solid was centrifuged, decanted, and dried in a vacuum oven at room temperature for 24 h. Since the polymer is photoactive, care is taken to keep it away from light. 1H NMR (DMSO-d6) δ 5.69 (d, J=37.47 Hz, 2H), 7.57 (m, 2H), 8.11 (m, 2H); 13C NMR (125 MHz, DMSO-d6) δ 46.1 (s), 69.2 (d), 115.9 (m), 125.6 (m), 130.8 (m), 163.2 (s), 190.8 (s).

II. Synthesis of Poly(2-(acetyloxy)-1-(4-hydroxyphenyl)-ethanone carbonate)-co-poly(ethylene glycol carbonate)

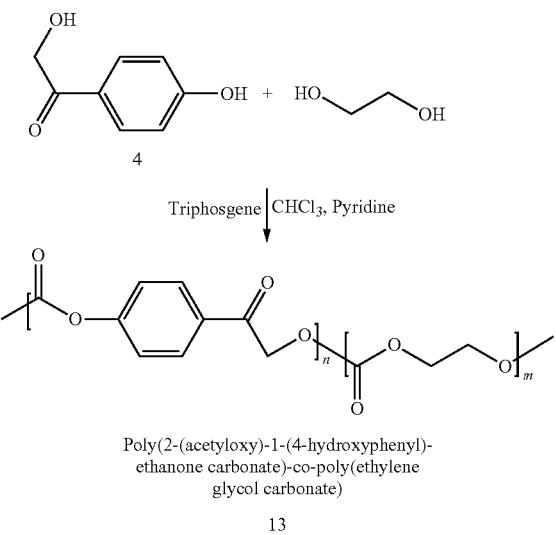

Poly(2-(acetyloxy)-1-(4-hydroxyphenyl)-ethanone carbonate)-co-poly(ethylene glycol carbonate)
13

4 (1 g, 6.6 mmol) and ethylene glycol (0.1 g, 1.6 mmol) were added to a two neck flask equipped with a stir bar. The flask was vacuumed and refilled with $N_2$ three times. Chloroform (10 ml) and pyridine (2.2 ml) were added. Then the solution was stirred and cooled with ice bath. In a small vial, triphosgene (0.89 g, 3.0 mmol) was dissolved in 5 ml chloroform. The triphosgene solution was added dropwise to the reaction mixture and almost immediately solid material started to precipitate. The reaction mixture was allowed to proceed for 2 hours, by the end of which the reaction temperature warmed up to room temperature. Then the polymer was precipitated in cold isopropanol (200 ml) and was obtained as a white solid. The solid was centrifuged, decanted, and dried in vacuum oven at room temperature for 24 h. Since the polymer is photoactive, care is taken to keep it away from light. 1H NMR (500 MHz, DMSO-d6) δ 4.34-4.61 (m, 0.75H), 5.54-5.83 (m, 2H), 7.40-7.68 (m, 2H), 8.01-8.20 (m, 2H); 13C NMR (125 MHz, DMSO-d6) δ 70.0 (d), 104.4 (s), 115.5 (d), 121.7 (m) 129.9 (m), 152.1 (s), 154.5 (m), 191.1 (d); IR (ATR) ν 3085, 2944, 1761, 1700, 1284, 1259, 1207, 1161, 960, 934, 837, 768 cm-1.

III. Synthesis of Poly(2-(acetyloxy)-1-(4-hydroxyphenyl)-ethanone-carbonate)-co-poly((poly(ethylene glycol)diol)carbonate)

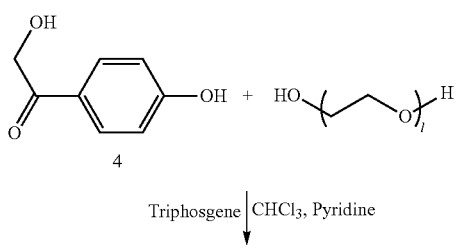

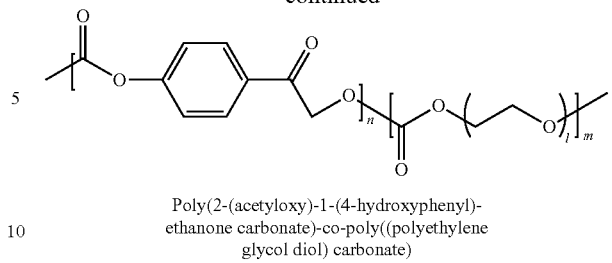

Poly(2-(acetyloxy)-1-(4-hydroxyphenyl)-ethanone carbonate)-co-poly((polyethylene glycol diol) carbonate)
14

4 (0.638 g, 4.2 mmol) and poly(ethylene glycol)diol (0.56 g, Mn 400 Da) were added to a two neck flask equipped with a stir bar. The flask was vacuumed and refilled with $N_2$ three times. Chloroform (10 ml) and pyridine (2.2 ml) were added. Then the solution was stirred and cooled with ice bath. In a small vial, triphosgene (0.621 g, 2.1 mmol) was dissolved in 5 ml chloroform. The triphosgene solution was added dropwise to the reaction mixture. The reaction mixture was allowed to proceed for 2 hours, by the end of which the reaction temperature warmed up to room temperature. Then the polymer was precipitated in cold isopropanol (200 ml) and was obtained as a white solid. The solid was centrifuged, decanted, and dried in vacuum oven at room temperature for 24 h. Since the polymer is photoactive, care is taken to keep it away from light. IR (ATR) ν 2949, 2913, 1759, 1258, 1207, 1169, 1098, 957, 839 cm-1.

IV. Synthesis of Poly(2-hydroxy-1-(4-(3-hydroxypropoxy)phenyl)ethanone carbonate)

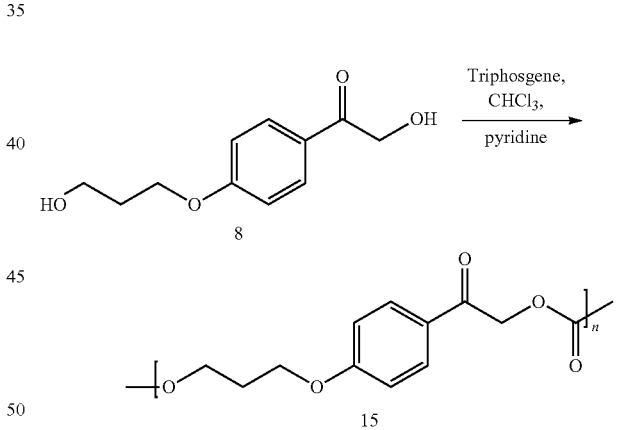

8 (0.76 g, 3.6 mmol) was added to a two neck flask equipped with a stir bar. The flask was vacuumed and refilled with $N_2$ three times. Chloroform (7 mL) and pyridine (1.8 mL) were added. Then the solution was stirred and cooled with ice bath. In a small vial, triphosgene (0.41 g, 1.38 mmol) was dissolved in 5 mL chloroform. The triphosgene solution was added dropwise to the reaction mixture. The reaction mixture was allowed to proceed for 2 hours, by the end of which the reaction temperature warmed up to room temperature. Then the polymer was precipitated in cold isopropanol (200 mL) and was obtained as a white solid. The solid was centrifuged, decanted, and dried in vacuum oven at room temperature for 24 h. Since the polymer was photoactive, care was taken to keep it away from light. 1H NMR (500 MHz, DMSO-d6) δ 2.10 (m, 2H), 4.16 (m, 2H), 4.27 (m, 2H), 5.48

(m, 2H), 7.07 (m, 2H), 7.91 (m, 2H); 13C NMR (125 MHz, DMSO-d6) δ27.8 (d), 64.4 (m), 68.8 (d), 114.5 (s), 126.5 (s), 130.0 (d), 154.3 (d), 162.8 (s), 190.7 (d); IR (ATR) v 2920, 1747, 1689, 1600, 1219, 1172, 1045, 948, 833, 752 cm-1.

V. Synthesis of Poly(2-hydroxy-1-(4-(3-hydroxypropoxy)phenyl)ethanone-carbonate)-co-poly((poly(ethylene glycol)diol)carbonate)

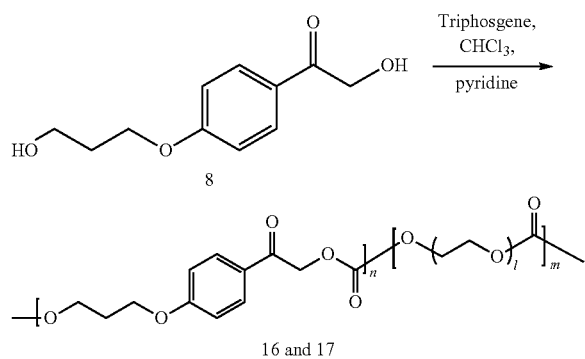

Low molecular poly(ethylene glycol) (PEG) (Mn 1000 Da, 0.36 g 0.36 mmol) and 8 (1.51 g, 7.18 mmol for 16 and 0.76 g, 3.6 mmol for 17) were added to a two neck flask equipped with a stir bar. The flask was vacuumed and refilled with $N_2$ three times. Chloroform (24 mL for 16 and 10 mL for 17) and pyridine (3.6 mL for 16 and 2 mL for 17) were added. Then the solution was stirred and cooled with ice bath. In a small vial, triphosgene (0.86 g, 2.89 mmol for 16 and 0.45 g, 1.53 mmol for 17) was dissolved in 5 mL chloroform. The triphosgene solution was added dropwise to the reaction mixture. The reaction mixture was allowed to proceed for 2 hours, by the end of which the reaction temperature warmed up to room temperature. Then the polymer was precipitated in cold isopropanol (200 mL) and was obtained as a white solid. The solid was centrifuged, decanted, and dried in vacuum oven at room temperature for 24 h. Since the polymer was photoactive, care was taken to keep it away from light. 1H NMR (500 MHz, $CDCl_3$) (12) δ 2.20 (d, J=22.00 Hz, 2H), 3.63 (s, 3.86H), 4.15 (d, J=26.19 Hz, 2H), 4.38 (d, J=40.85 Hz, 2H), 5.30 (d, J=33.52 Hz, 2H), 6.92-6.97 (m, 2H), 7.83-7.90 (m, 2H); 13C NMR (125 MHz, CDCl3) δ 28.5 (d), 64.5 (m), 68.8 (d), 70.5 (d), 114.6 (m), 130.0 (d), 154.8 (d) , 163.4 (s); IR (ATR) v 2937, 2881, 1745, 1691, 1598, 1425, 1259, 1224, 1172, 1116, 1051, 950, 835, 788 cm-1.

Analysis of Polymer Chain Photodegradation with Time of Irradiation:

The photodegradable polymer 15 (20 mg) was dissolved in chloroform (10 mL, HPLC grade, EMD Omnisolv™) and transferred to a quartz tube (diam=12 mm) The quartz tube was sealed with a rubber septum and irradiated in a Rayonet™ RPR-200 reactor at 300 nm where the polymer has a significant UV absorption (5.34 mW/cm2). Every 5 minutes (with an error of about 5 s), the reactor was turned off; 1 mL of reaction mixture was taken out and filtered through a 0.45 micron PTFE filter. 9 samples were taken in 40 minutes of irradiation and the rest of the solution was irradiated for an extra hour, filtered through a 0.45 micron PTFE filter and collected as the last sample. All sample analysis were done on a TOSOH™ EcoSec HLC-8320 GPC equipped with one TSK-GEL™ super H 4000 column and two TSK-GEL™ super H 3000 columns, using the same chloroform mentioned above as eluent. Photodegradation of 16 and 17 were analyzed by this same method.

UV-Vis Spectrum of Polymer with Time of Irradiation:

Polymer 15 was dissolved in chloroform and transferred to a fluorescence quartz cuvette and degassed. UV spectrum of the sample was taken and then irradiated in the Rayonet reactor at 300 nm. After every one minute, the reactor was turned off, and the UV spectrum was recorded, for a total time of 10 minutes.

Estimation of Quantum Yield of Photodegradation:

In a fluorescence quartz cell, 1.3 mg polymer 15 was dissolved in 1 mL $CDCl_3$ along with 4 µL methyl succinate as an internal standard, and 10 µL CD3OD. The solution was purged with Ar and sealed. The dimensions of the cell were 0.94 cm by 0.94 cm and the height of the solution was 0.71 cm. The sample was irradiated for 3 minutes and analysis of the reaction by 1H NMR showed 9.1% conversion of the polymer. The light intensity under the experimental conditions is 5.34 mW/cm2 at 300 nm. From these values the quantum yield was determined to be 0.078.

Fabrication of Micro-patterned Surfaces:

A thin photodegradable polymer film was spin coated onto a clean silicon substrate from a 20 mg/mL polymer solution of 15 in chloroform at 3000 rpm. A 1000 mesh copper TEM grid was placed over the film as a photo-mask. A quartz plate was placed over the TEM grid. The above assembly was irradiated for 30 minutes in the Rayonet™ RPR-200 reactor. Following the irradiation, the quartz plate and TEM grid were removed and the film was washed with methanol to remove the degraded polymer. The micro-patterns on the film were characterized by optical microscopy, SEM and AFM.

TABLE 1

Physical properties of the homopolymer and copolymers

| Composition | Mn (g/mol)a | Mw (g/mol)a | PDIa | Tg (° C.)b | Td (° C.)c | Modulus, E (MPa)d | Stress at yield (σy), MPa | Strain at yield (εy), % |
|---|---|---|---|---|---|---|---|---|
| Homopolymer (15) | 12900 | 29525 | 2.3 | 63 | 271 | — | — | — |
| 5% PEG1k (16) | 22698 | 26252 | 1.2 | 9 | 250 | 173 | 8.5 | 14 |
| 10% PEG1k (17) | 8810 | 10352 | 1.2 | 1 | 248 | 59 | 4.9 | 22 | aResult from GPC;
bResult from DSC;
cResult from TGA;
dResult from uniaxial tension Modulus Measurements Tensile modulus was measured in the Applied Polymer Research Center at The University of Akron. Specimens were cut into 10 mm long, 4 mm wide, and 0.06 mm thick samples. The samples were measured under uniaxial tension at 0.04 mm/s Thermal Stability of Polymers 100 mg of polymer 16, was compressed as a pellet and heated between two aluminum molds to 180° C. It was held at this temperature for 1 h and then the polymer was dissolved and analyzed by 1H NMR.

Hydrolytic Degradation of Polymers 5 mL of 10×PBS solution was diluted with 45 mL deionized water. 75 mg each of polymers 16 and 17, were dissolved in 1 mL $CHCl_3$. The solution was stirred for few hours to allow the polymer to dissolve in the solvent completely. Polymer films were prepared by solvent casting the above solution into a Teflon dish and allowing the solvent to evaporate slowing overnight and were dried under vacuum prior to use. Hydrolytic degradation was monitored by immersing half of each polymer film (~36 mg) in a vial containing 5 mL of the above 1×PBS solution. Each vial was kept in the incubator at 37° C. At the end of every week (total of 4 weeks) a small piece of film was taken from the vial, dried, dissolved in chloroform and analyzed by GPC.

Release of Nile Red from Polymer Nanoparticles 10 mg polymer 16 and 0.1 mg Nile Red were dissolved in 1 mL DMSO. A quartz tube (diam=12 mm) containing 10 mL of water was sealed with a rubber septum, and then purged with Ar for 10 minutes. 0.3 ml of the above polymer solution was filtered, added to the rapidly stirred water in the above quartz tube. No aggregation or precipitation was observed. The nanoparticles had a distribution between 50 to 500 nm as shown by light scattering, and supported by TEM experiments. The quartz tube was then irradiated in the Rayonet® RPR-200 reactor, at 300 nm (5.34 mW/cm$^2$). At defined time points, the reactor was turned off, and 0.3 ml solution was taken out as a sample. The first sample was taken before irradiation. Fluorescence spectra of all the samples were recorded.

In a separate study instead of fluorescence, UV spectrum of the solution was taken. The nanoparticle solution was prepared as described above and sealed in a fluorescence quartz cell, and the UV spectrum was recorded. Then the quartz cell was irradiated at 300 nm (5.34 mW/cm$^2$) in a Rayonet™ RPR-200 reactor and. At defined time points, the reactor was turned off, the cell was taken out and UV spectrum was recorded.

For the control experiment, Nile Red was dissolved in 1:1 THF: water, purged with Ar for 10 minutes and sealed in a fluorescence quartz cell and the UV spectrum was recorded. Then the quartz cell was irradiated at 300 nm (5.34 mW/cm$^2$). At defined time points, the reactor was turned off, the cell was taken out and UV spectrum was recorded.

Discussion

The homopolymer and different copolymers with PEG (Table 1) were synthesized and characterized by NMR and gel permeation chromatography (GPC). PEG copolymers are used in biomedical applications as PEG decreases nonspecific protein adsorption and also decreases the Tg of the polymer. These polymers have UV absorption from 250 to 320 nm with a λmax at 280 nm. The extinction coefficient of the homopolymer is 0.79×04 M-1 cm-1 (calculated with respect to the photoactive unit) which is comparable to the values of hydroxyphenacyl esters (1.4×104 M-1 cm-1).

Photodegradation of the polymers was examined by irradiation in $CHCl_3$ in a Rayonet reactor at 300 nm (16 tubes, 5.34 mW/cm$^2$). GPC traces of the irradiated samples of the homopolymer (FIG. 1) showed that the polymer underwent controlled time-dependent chain scission upon irradiation. Within 5 min of irradiation, there was a loss of three-fourths of the molecular weight (MW) of the polymer. Further experiments confirmed that all the three polymers listed below undergo similar photodegradation. The UV spectrum of the photodegradation products also shows the expected change in λmax upon irradiation as a result of the phenacyl moiety rearranging to the blue-shifted phenyl acetic acid derivative.

NMR spectroscopy, of irradiation of the copolymer 16, showed the appearance of new peaks at 4.8, 3.8, and 2.5 ppm and a decrease of the number of protons corresponding to the CH2 α to the ketone (5.37 ppm).

As expected, the rate of photodegradation in the solid state was substantially slower than solution photodegradation. While it was difficult to quantify the solid state degradation products (due to their low concentration) it is clear, as detailed below, that the expected photodegradation occurs in the solid state as shown by the results from irradiation of films and nanoparticles of these materials.

A key attribute of these polymers is their thermal stability (Table 1) which would allow the use of high temperature fabrication methods such as compression molding and extrusion. The homopolymer 15 has a decomposition temperature of 271° C. and a Tg of 63° C. To further assess the thermal stability of these polymers, the copolymer 16 was molded as a pellet and held at 180° C. for 1 h. The NMR spectrum of this sample was essentially identical to that of the sample prior to heating, demonstrating the stability of these polymers to high temperature.

The tensile moduli of the copolymers (with 5 mol % and 10 mol % PEG) were evaluated by uniaxial tensile tests and showed moduli of 173 MPa and 59 MPa, respectively. As a comparison, the Young's modulus of low density polyethylene is about 300 MPa, and that for poly[(lactic acid)0.5-co-(glycolic acid)0.5] is 1 GPa0.26 The elastic moduli of the current materials indicate that they can be used for biomedical devices that do not bear high loads. The strain at yield ($\epsilon y$) is sufficient to prevent fracture during normal bending.

Figure 3:
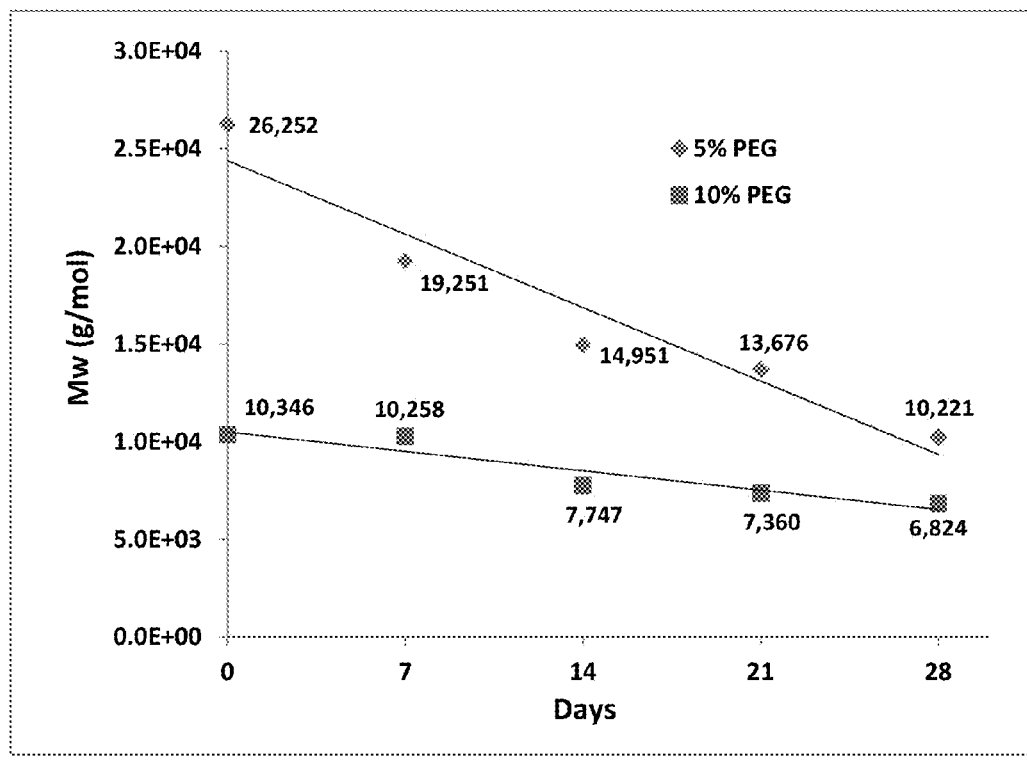
FIG. 3 is a graph of hydrolytic degradation of copolymers 16 (5% PEG) and 17 (10% PEG)

Incubation of the copolymers 16 and 17 in phosphate buffered saline (PBS) at 37° C. leads to hydrolytic degradation as reflected by the molecular weight loss with the time of incubation. For example, over a period of 28 days, the copolymer with 5% PEG showed increasing molecular weight loss with time and ultimate loss of 61% of molecular weight on day 28 (FIG. 3). As expected, the photochemical degradation is much faster—the polymer undergoes almost complete photodegradation within 30 min (FIG. 1), while hydrolytic degradation over 28 days results in a 61% loss for the 5% PEG copolymer.

Controlled delivery of therapeutics from polymeric devices is a promising strategy to increase the bioavailability and decrease drug dosage. In general, drug release from controlled delivery devices occurs by diffusion or is assisted by hydrolytic degradation of the matrix. Compared to traditional dermal patches, it is likely that in these devices the dose can be controlled by the intensity and time of irradiation. As a proof of concept, Nile Red release from nanoparticles of the copolymer with 5% PEG was examined Nile Red has been used as a model compound in several controlled release studies.

Figure 4:
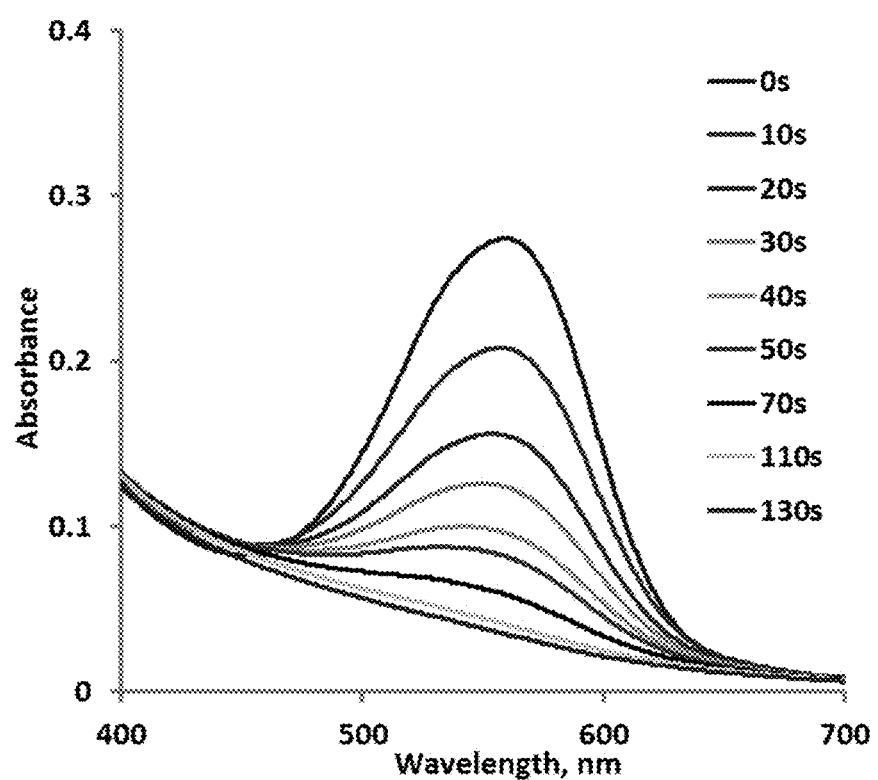
FIG. 4 is a graph showing the decrease in absorbance of due to the release of Red Nile from photoirradiated nanoparticles of copolymer 16 (5% PEG)
Figure 5:
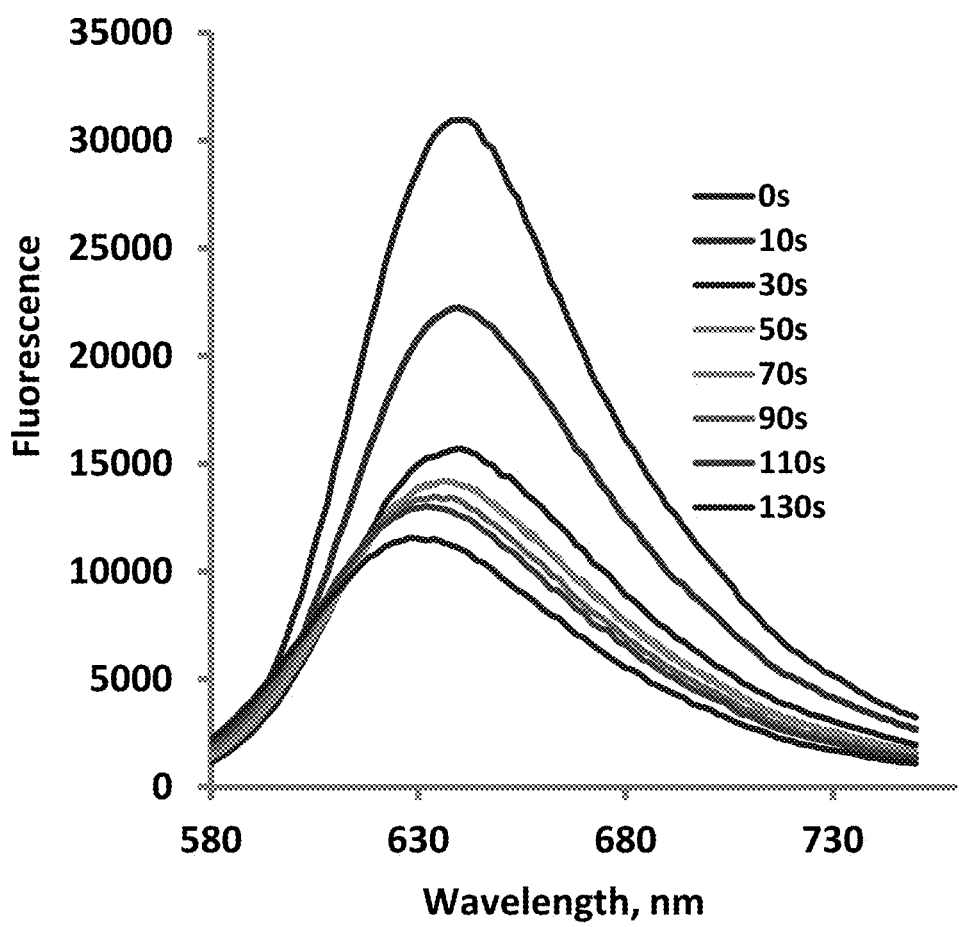
FIG. 5 is a graph showing the decrease in fluorescence intensities due to the release of Red Nile from photoirradiated nanoparticles of copolymer 16 (5% PEG)
Figure 6:
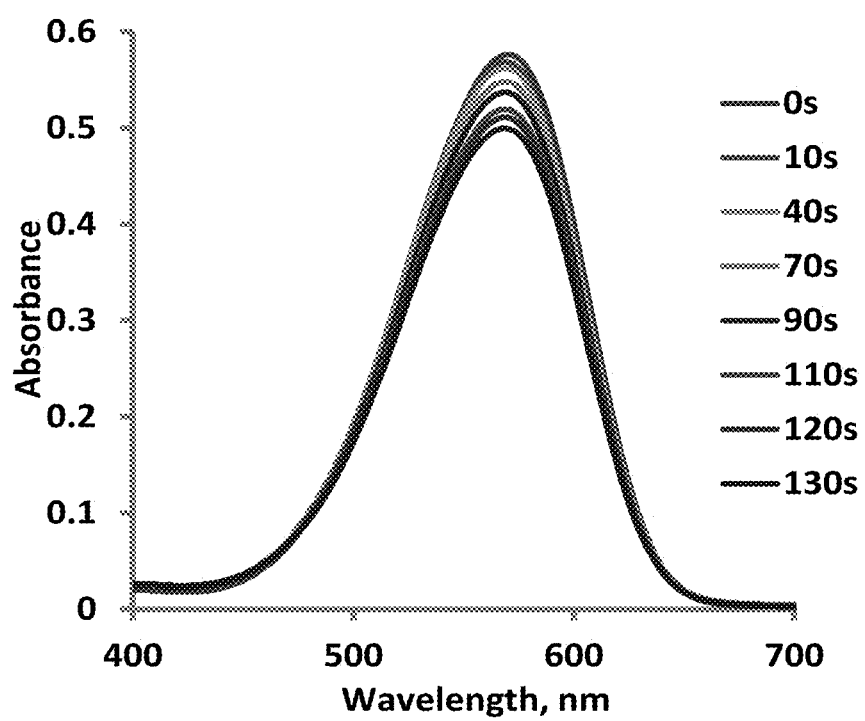
FIG. 6 is a graph of absorbance of photoirradiated Nile Red in 1:1 THF:water, provided as a control.

Aqueous solutions of Nile Red encapsulated nanoparticles were pink and showed the expected fluorescence. Nile Red was released by brief irradiation (0-130 s) and resulted in a decrease of absorbance and fluorescence intensities due to the insolubility of Nile Red in water (FIGS. 4-6). Nile Red photobleaches upon extended irradiation but is reasonably stable during the time frame of these experiments (130 s). As a control, irradiation of Nile Red in 1:1 THF:water showed only a slight decrease in absorbance compared to the results for irradiation within the nanoparticles. Currently, there is the limitation that these materials can only be used in applications accessible to 270-320 nm light such as in topical dressings, cosmetics, and ocular implants.

Micropatterned surfaces are useful in numerous applications and are of special utility in studying the fundamental aspects of cell-cell and cell-material signaling. Various cell types are influenced by patterned substrates, and micropatterned surfaces allow tissue-like conditions to be reconstructed and examined in vitro. The photodegradable polycarbonates discussed here can be used to create such micropatterned surfaces which may find utility in biomedical applications. As a proof of concept, polymer films (150-200 nm thick) coated on silicon were irradiated through a 1000 mesh transmission electron microscopy (TEM) grid for 30 min and washed thoroughly with MeOH. As shown by AFM, the TEM grid pattern was reproduced on the polymer films. The ridges were 6 μm across, and the degraded squares were 19 μm on each side. These dimensions correspond to the measurements of the TEM grid. The irradiation caused the polymer to degrade away to a depth of about 120 nm. The SEM results also corroborated the images obtained by AFM and show a larger area of the patterned surface. We are currently working toward translating this patterning process to thicker polymer films with features of about 1 micrometer depth and 10-20 μm wide. Nerve guidance conduits and small diameter vessels are critical needs in tissue engineering. Although the results demonstrated here are premature for such applications, the use of these photoresponsive materials for creating mico-patterned surfaces for these applications is promising and is currently being explored.

These examples thus provide the synthesis and properties of a new class of photodegradable polymers that undergo controlled chain scission upon photoirradiation. The results demonstrate that the polymers quickly lose their molecular weight upon irradiation but are stable to high temperatures in the absence of light. In addition, these polymers are mechanically robust and biodegradable. These combined properties make them very valuable for many biomedical applications. For example, controlled drug delivery devices such as ocular implants and dermal patches could potentially be designed from such polymers. In addition, polymeric 2D and 3D structures with micropatterned architecture can potentially be fabricated from such polymers.

Photoresponsive Polyester Polymers

I. Synthesis of Poly(2-(4-(2-hydroxyacetyl)phenoxy)acetic acid)

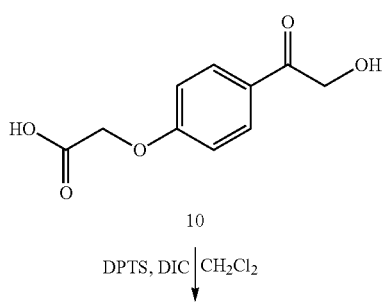

10

DPTS, DIC | CH2Cl2

-continued

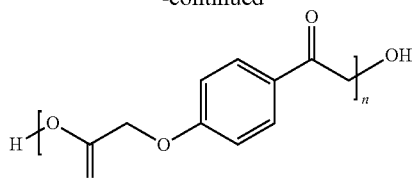

Poly(2-(4-(2-Hydroxyacetyl)phenoxy)acetic acid)

18

10 (0.2 g, 0.8 mmol) and 4-(N,N-dimethylamino)pyridinium-4-toluenesulfonate (DPTS) (0.05 g, 0.16 mmol) were taken in a two neck flask equipped with a stir bar. The flask was vacuumed and refilled with N₂ three times. The flask was cooled with an ice bath. Dichloromethane (2 ml), dimethylformamide (DMF) (0.2 ml) and N,N'-Diisopropylcarbodiimide (DIC) (0.19 ml, 0.15 g, 1.2 mmol, 1.5 eq) were added. The reaction mixture was allowed to polymerize for 48 hours, during which time a lot white solid came out. The resulting polymer was precipitated in methanol (100 ml). The polymer was collected and dried in vacuum oven, and was obtained as a white solid. IR (ATR) ν 3341, 2073, 2937, 1767, 1688, 1600, 1202, 1167, 1121, 1082, 1078, 968, 833, 810 cm-1.

II. Synthesis of Poly(2-hydroxy-1-(4-(3-hydroxypropoxy)phenyl)ethanone adipate)

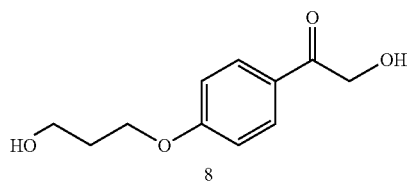

8

Adipic acid | CH2Cl2
DPTS, DIC

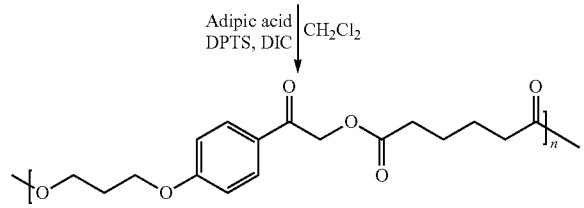

Poly(2-Hydroxy-1-(4-(3-hydroxypropoxy)phenyl)ethanone adipate)

19

Adipic acid (0.5 g, 2.9 mmol), 8 (0.61 g, 2.9 mmol) and 4-(N,N-dimethylamino)pyridinium-4-toluenesulfonate (DPTS) (0.34 g, 1.2 mmol) were taken in a two neck flask equipped with a stir bar. The flask was vacuumed and refilled with N₂ three times. The flask was cooled with an ice bath. Dichloromethane (3 ml) and diisopropylcarbodiimide (DIC) (1.36 ml, 1.1 g, 8.7 mmol, 3 eq) were added. The reagents were allowed to polymerize for 48 hours. The resulting polymer was precipitated in methanol (100 ml). The polymer was collected, dried in vacuum oven and was obtained as a white solid. 1H NMR (500 MHz, DMSO-d6) δ 1.59 (t, J=39.52 Hz, 4H), 2.05 (m, 2H), 2.26-2.36 (m, 2H), 2.40-2.48 (m, 2H) 4.10-4.20 (m, 4H), 5.40 (d, J=9.61 Hz, 2H), 7.05 (br, 2H), 7.88-7.94 (m, 2H); 13C NMR (125 MHz, DMSO-d6) δ 23.7 (m), 27.8 (d), 32.8 (m), 60.5 (s), 65.1 (d), 114.4 (s), 126.7 (s), 130.0 (d), 162.7 (s), 172.5 (m), 190.9 (s); IR (ATR) ν 2967, 2939, 1161, 1237, 1731, 1692, 1602, 1119, 1057, 969, 952, 832, 644 cm-1.

Photoresponsive Side Chain

I. Synthesis of Photoresponsive Drug Delivery Molecule

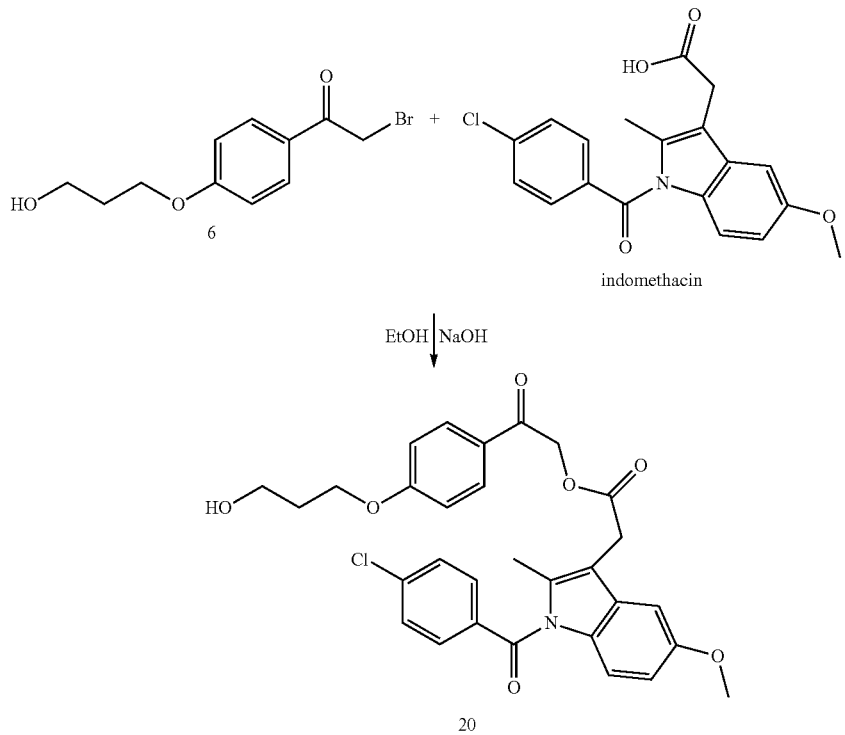

Indomethacin (2.0 g, 5.7 mmol) was dissolved in ethanol (5 ml). NaOH (0.21 g, 5.2 mmol) was dissolved in water (5 ml) and slowly added into the above solution. The mixture was stirred for 10 minutes. 6 (1.3 g, 4.8 mmol) was dissolved in ethanol (5 ml) and added to the above solution. The mixture was refluxed for 3.5 hours. The solvent was removed and the remaining was distributed between water (30 ml) and ethyl acetate (30 ml). The water layer was extracted with ethyl acetate (30 ml each time, 2 times). The combined organic solution was dried over sodium sulfate and removed to get the crude product. The product was recrystallized from ethyl acetate and hexane to give pure product (1.7 g, 3.1 mmol, 64.6% yield). 1H NMR (300 MHz, CDCl$_3$) δ ppm 2.00-2.17 (m, 2 H) 2.38 (s, 3 H) 3.69-3.93 (m, 3 H) 4.18 (t, J=6.00 Hz, 2 H) 5.30 (s, 2 H) 6.65-6.71 (m, 1 H) 6.84-6.97 (m, 3 H) 7.06 (d, J=2.63 Hz, 1 H) 7.44-7.58 (m, 2 H) 7.63-7.72 (m, 2 H) 7.80-7.92 (m, 2 H).

II. Synthesis of Monomer of Photoresponsive Molecule

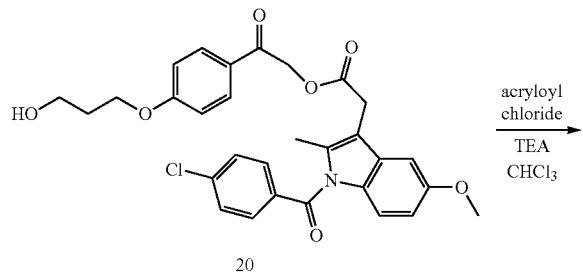

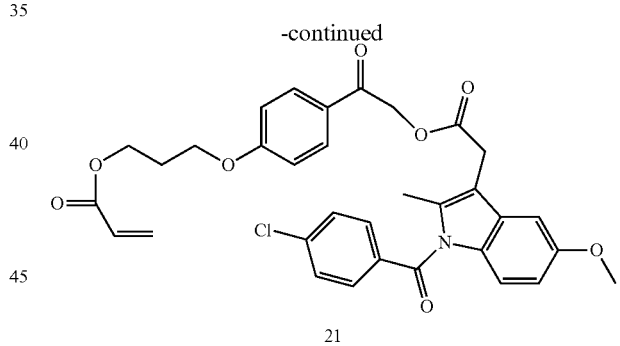

20 (1.7 g, 3.1 mmol) and triethyl amine (0.60 ml, 4.3 mmol) was dissolved in CHCl$_3$ (12 ml) and cooled in ice bath. Acryloyl chloride (0.3 1, 3.7 mmol) was added into the above solution dropwise. The reaction was stirred for 4 hours. Then water was added to quench the reaction. The organic phase was separated, dried over sodium sulfate, and removed to get the crude product. Further purification was performed by column chromatography (50% ethyl acetate-50% hexane) to give the pure product as a white powder (1.4 g, 2.3 mmol, 75% yield). 1H NMR (300 MHz, CDCl$_3$) d ppm 2.15-2.36 (m, 2 H) 2.40 (s, 1 H) 3.44-3.75 (m, 3 H) 3.75-3.99 (m, 2 H) 4.03-4.25 (m, 2 H) 4.26-4.47 (m, 2 H) 5.26-5.39 (m, 2 H) 5.84 (dd, J=10.54, 1.46 Hz, 1 H) 6.15 (d, J=10.54 Hz, 1 H) 6.42 (dd, J=17.27, 1.46 Hz, 1 H) 6.68 (dd, J=8.93, 2.49 Hz, 1 H) 6.85-7.02 (m, 3 H) 7.06 (d, J=2.63 Hz, 1 H) 7.44-7.50 (m, 2 H) 7.61-7.72 (m, 2 H) 7.79-7.92 (m, 2 H)

III. Synthesis of Polymer with Side Chain Photoresponsive Drug Molecule

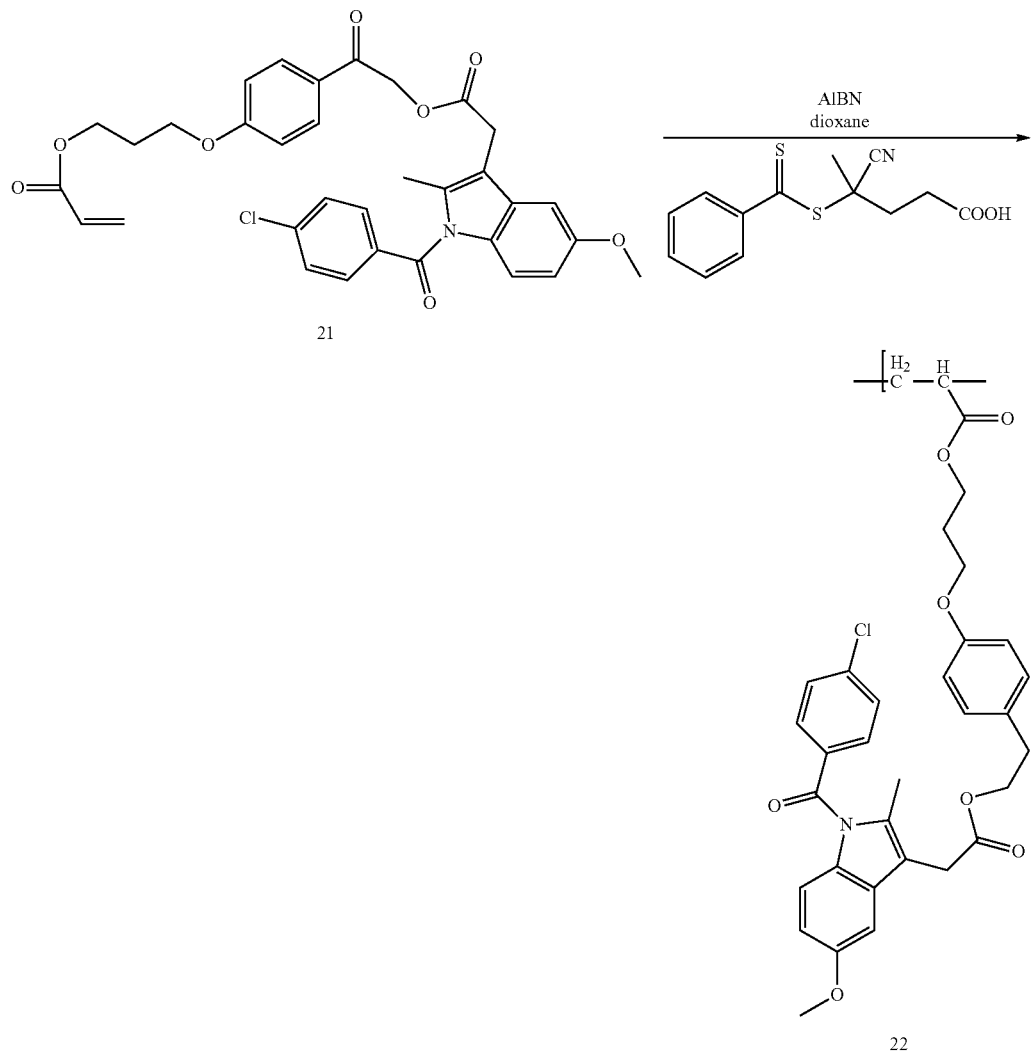

21 (0.884 g, 1.46 mmol), azodiisobutyronitrile (AIBN, 0.002 g, 00012 mmol), and RAFT reagent (0.014 g, 0.049 mmol) was dissolved in dioxane (6 ml) and three freeze-pump-thorn circles were performed. The reaction was heated to 70° C. for 6 hours. Then it was precipitated in Et$_2$O, centrifuged, redissolved in dioxane, and precipitated in Et$_2$O again to get pure polymer product. MALDI-MS showed repeating structure molecular mass of 603.4 g/mol (calculated: 603.2 g/mol).

What is claimed is:

1. A substituted phenacyl composition of matter according to the following structure:

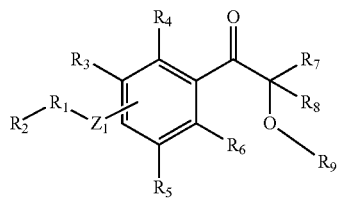

wherein $R_1$ is an alkyl chain of from C1 to C10; $R_2$ is —COOH; $R_3$ through $R_9$ are hydrogen, and $Z_1$ is at the para-position and is O; or wherein R1 is an alkyl chain of from C1 to C10; $R_2$ is a group of atoms containing at least one functional group; $R_3$ through $R_8$ are selected from H, Cl, Br, F, alkyl, vinyl, alkynyl, aryl, or alkoxy groups, O—$R_9$ is selected from an ester group, a carbonate group, a phosphate group, a sulfate group and sulfinate group, and $Z_1$ may be at the ortho-, meta- or para-position and is selected from O, S, HNC=O or $R_{10}$NC=O, wherein $R_{10}$ is selected from any atom or group of atoms.

2. The composition of claim 1, wherein $R_1$ an alkyl chain of from C1 to C10, $R_2$ is —COOH, and $Z_1$ is oxygen.

3. The composition of claim 2, wherein $R_1$ is CH$_2$.

4. The composition of claim 1, wherein $R_3$ through $R_8$ are selected from H, Cl, Br, F, alkyl, vinyl, alkynyl, aryl, or alkoxy groups, O—$R_9$ is selected from an ester group, a carbonate group, a phosphate group, a sulfate group and sulfinate group.

5. A polymer, macromolecule, copolymer, oligomer, dendrimer, dendron, or macrocycle that includes one or more following structural unit(s):

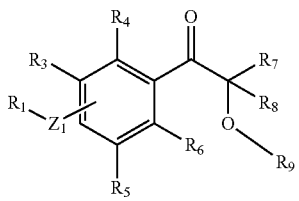

wherein $R_1$ is a bond or an alkyl chain of from C1 to C10; $R_3$, $R_4$, $R_5$, $R_6$, $R_7$, and $R_8$ may be any atom or group of atoms; $Z_1$ may be at the ortho, meta or para position and is selected from O, S, HNC=O or $R_{10}$NC=O, wherein $R_{10}$ is selected from any atom or group of atoms; and wherein (a) $R_9$ is selected from RC=O, wherein R represents any substitution, or (b) O—R9 is selected from an ester group, a carbonate group, a phosphate group, a sulfate group and sulfinate group.

6. The composition of matter of claim 5, wherein $R_9$ is selected from RC=O, wherein R represents any substitution.

7. The composition of matter of claim 5, wherein O—$R_9$ is selected from an ester group, a carbonate group, a phosphate group, a sulfate group and sulfinate group.

8. The composition of matter of claim 7, wherein $R_3$ through $R_8$ are hydrogen, and $Z_1$ is oxygen and is at the para position.

9. The composition of matter of claim 5, wherein $R_1$ is a bond, $R_9$ is the next repeating unit, and the composition is a polycarbonate homopolymer having the following structure:

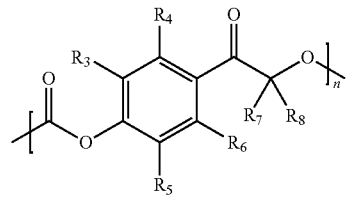

wherein $R_3$ through $R_8$ may be any atom or group of atoms and n is any number of repeating units.

10. The polycarbonate polymer of claim 9, wherein $R_3$ through $R_8$ are hydrogen.

11. The composition of matter of claim 5, wherein the composition is a polycarbonate polymer having the following structure:

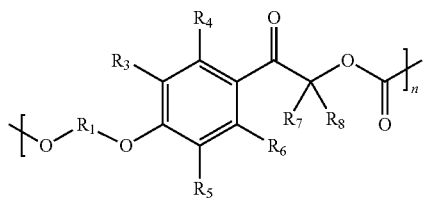

wherein $R_1$ is alkyl chain of from C1 to C10; $R_3$, $R_4$, $R_5$, $R_6$, $R_7$, and $R_8$ may be any atom or group of atoms, n is any number of repeating units.

12. The polycarbonate polymer of claim 11, wherein $R_1$ is a propylene chain ($C_3H_6$) and $R_3$ through $R_8$ are hydrogen.

13. The composition of matter of claim 5, wherein the composition is a polycarbonate copolymer having the following structure:

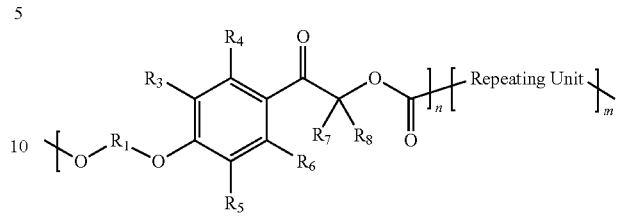

wherein $R_1$ is alkyl chain of from C1 to C10; $R_3$, $R_4$, $R_5$, $R_6$, $R_7$, and $R_8$ may be any atom or group of atoms; n is any number of repeating units; "Repeating Unit" is a repeating unit contributed by a comonomer or copolymer; m is any number of repeating units; wherein the n and m repeating units are in statistical arrangement.

14. The polycarbonate copolymer of claim 13, wherein $R_1$ is a propylene chain ($C_3H_6$) and $R_3$ through $R_8$ are hydrogen.

15. The composition of matter of claim 5, wherein the composition is a polyester polymer comprising the following structure:

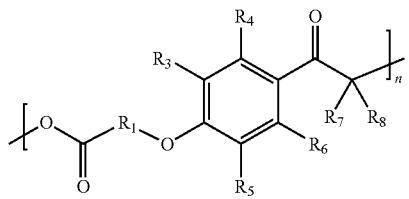

wherein $R_3$, $R_4$, $R_5$, $R_6$, $R_7$, and $R_8$ may be any atom or group of atoms, $R_1$ is an alkyl chain of from C1 or more to C10 or less, and n represents any number of repeating units.

16. The polyester polymer of claim 15, wherein $R_3$ through $R_8$ are hydrogen and $R_1$ is methylene ($CH_2$).

17. The polyester polymer of claim 15, wherein the polymer is a copolymer comprising the structure thereof as part of the polymer.

18. The composition of matter of claim 5, wherein the composition is a polyester polymer comprising the following structure:

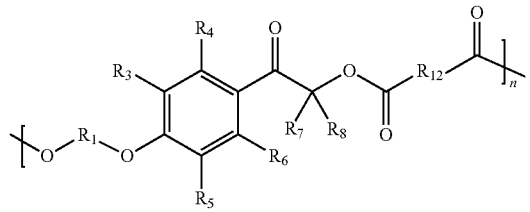

wherein $R_3$, $R_4$, $R_5$, $R_6$, $R_7$, and $R_8$ may be any atom or group of atoms, $R_1$ is an alkyl chain of from C1 to C10, $R_{12}$ is either a bond between the two carbonyl groups or is an alkyl chain of from C1 to C10, and n is any number of repeating units.

19. The polyester polymer of claim 18, wherein $R_{3\ through}$ $R_8$ are hydrogen, $R_1$ is a propylene chain ($C_3H_6$) and $R_{12}$ is a butylene chain ($C_4H_8$).

20. The polyester polymer of claim 18, wherein the polymer is a copolymer comprising the structure thereof as part of the polymer.

21. The composition of matter of claim 5, wherein $R_1$ links the structural unit thereof to a polymer chain, and $R_9$ is part of a drug molecule, part of an additive, or part of a sensitizer.

22. The composition of matter of claim 5, wherein $R_1$ and $R_9$ individually links the structural unit thereof to a polymer chain, and the structural unit thereof serves as a linker of the polymer chains, wherein the polymer chains could be same or different.

* * * * *